(12) United States Patent
Yuen et al.

(10) Patent No.: US 12,379,331 B2
(45) Date of Patent: Aug. 5, 2025

(54) SINGLE SHOT ANALYZER GRATING FOR DIFFERENTIAL PHASE CONTRAST X-RAY IMAGING AND COMPUTED TOMOGRAPHY

(71) Applicant: The Board of Trustees of the Leland Stanford Junior University, Stanford, CA (US)

(72) Inventors: Max Yuen, San Francisco, CA (US); Yao-Te Cheng, Sunnyvale, CA (US); Paul Christopher Hansen, Palo Alto, CA (US); Lambertus Hesselink, Atherton, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 322 days.

(21) Appl. No.: 17/639,558

(22) PCT Filed: Sep. 4, 2020

(86) PCT No.: PCT/US2020/049554
§ 371 (c)(1),
(2) Date: Mar. 1, 2022

(87) PCT Pub. No.: WO2021/046458
PCT Pub. Date: Mar. 11, 2021

(65) Prior Publication Data
US 2022/0341856 A1 Oct. 27, 2022

Related U.S. Application Data

(60) Provisional application No. 62/897,011, filed on Sep. 6, 2019.

(51) Int. Cl.
*G01N 23/041* (2018.01)
*G01N 23/046* (2018.01)
(Continued)

(52) U.S. Cl.
CPC ......... *G01N 23/041* (2018.02); *G01N 23/046* (2013.01); *G01N 23/083* (2013.01);
(Continued)

(58) Field of Classification Search
CPC .. G01N 23/041; G01N 23/046; G01N 23/083; G01N 2223/04; G01N 2223/30;
(Continued)

(56) References Cited

U.S. PATENT DOCUMENTS 10,058,300 B2 * 8/2018 Baturin ................ A61B 6/4035
2010/0322380 A1 * 12/2010 Baeumer ................. G21K 1/06
250/336.1
(Continued)

FOREIGN PATENT DOCUMENTS

WO    WO-2017036726 A1 * 3/2017 ............. A61B 6/484

OTHER PUBLICATIONS

Chen et al. "Single-shot grating-based x-ray differential phase contrast imaging with modified analyzer grating", IOP Publishing Ltd, Chin. Phys. B vol. 26, No. 10, 2017, p. 108701-1-108701-8 (Year: 2017).*

(Continued)

*Primary Examiner* — David P Porta
*Assistant Examiner* — Mamadou Faye
(74) *Attorney, Agent, or Firm* — Beyer Law Group LLP

(57) ABSTRACT

In accordance with the invention, an X-ray amplitude analyzer grating adapted for use in an interferometric imaging system, the interferometric imaging system comprising an X-ray source and an X-ray detector with an X-ray fringe plane between the X-ray source and the X-ray detector, wherein an X-ray fringe pattern is formed at the X-ray fringe plane, wherein the X-ray amplitude analyzer grating is provided. The X-ray amplitude analyzer grating comprises a plurality of grating pixels across two dimensions of the
(Continued)

X-ray amplitude analyzer grating, wherein each grating pixels of the plurality of grating pixels has a different pattern with respect to all adjacent grating pixels to the grating pixel so that all adjacent grating pixels do not have a same pattern as the grating pixel.

31 Claims, 31 Drawing Sheets

(51) Int. Cl.
*G01N 23/083* (2018.01)
*G06T 11/00* (2006.01)

(52) U.S. Cl.
CPC ........ *G06T 11/008* (2013.01); *G01N 2223/04* (2013.01); *G01N 2223/30* (2013.01); *G01N 2223/401* (2013.01); *G01N 2223/419* (2013.01)

(58) Field of Classification Search
CPC ........ G01N 2223/401; G01N 2223/419; G06T 11/008; A61B 6/032; A61B 6/4291; A61B 6/484; G21K 2207/005; G21K 1/025; G01V 5/005
See application file for complete search history.

(56) References Cited

U.S. PATENT DOCUMENTS

| | | | |
|---|---|---|---|
| 2012/0153177 A1 | 6/2012 | Iwakiri | |
| 2012/0163541 A1 | 6/2012 | Kaneko | |
| 2012/0236985 A1* | 9/2012 | Schusser | A61B 6/484 378/62 |
| 2013/0010926 A1 | 1/2013 | Tada | |
| 2013/0051519 A1* | 2/2013 | Yang | G06T 11/005 378/19 |
| 2013/0208864 A1* | 8/2013 | Rossl | A61B 6/484 250/394 |
| 2014/0226783 A1* | 8/2014 | Ning | A61B 6/502 378/19 |
| 2014/0270456 A1* | 9/2014 | Khare | G06T 5/70 382/133 |
| 2014/0294148 A1 | 10/2014 | Bernhardt et al. | |
| 2014/0341347 A1 | 11/2014 | Radicke | |
| 2015/0071402 A1* | 3/2015 | Handa | G01N 23/20075 378/71 |
| 2018/0140269 A1* | 5/2018 | Roessl | A61B 6/032 |
| 2018/0246046 A1* | 8/2018 | Kagias | A61B 6/484 |
| 2019/0219713 A1 | 7/2019 | Steadman Booker et al. | |
| 2019/0317027 A1* | 10/2019 | Tsuboi | G01N 23/041 |
| 2019/0355488 A1* | 11/2019 | Koehler | G21K 1/025 |
| 2020/0111194 A1* | 4/2020 | Wang | G06N 3/047 |

OTHER PUBLICATIONS

International Search Report from International Application No. PCT/US2020/049554 dated Nov. 24, 2020.
Written Opinion from International Application No. PCT/US2020/049554 dated Nov. 24, 2020.
Bradley T. Kimbrough, Pixelated mask spatial carrier phase shifting interferometry algorithms and associated errors, Applied Optics, vol. 45, No. 19, Jan. 24, 2006.
M. Servin et al., Fourier transform demodulation of pixelated phase-masked interferograms, Optics Express, vol. 18, No. 15, Jul. 15, 2010.
M. Servn et al., Error-free demodulation of pixelated carrier frequency interferograms, Optics Express, vol. 18, No. 17, Aug. 13, 2010.
J.M.Padilla et al., Synchronous phase-demodulation and harmonic rejection of 9-step pixelated dynamic interferograms, Optics Express, vol. 20, No. 11, May 9, 2012.
Tatsuki Tahara et al., Algorithm for reconstructing wide space-bandwidth information in parallel two-step phase-shifting digital holography, Optics Express, vol. 20, No. 18, Aug. 14, 2012.
Orlando Medina et al., Robust adaptive phase-shifting demodulation for testing moving wavefronts. Optics Express. vol. 21, No. 24, Nov. 22, 2013.
Ruihua Zhang et al., Phase gradients from intensity gradients; a method of spatial carrier fringe pattern analysis, Optics Express, vol. 22, No. 19, Sep. 10, 2014.
Tatsuki Tahara et al., Spatial-carrier phase-shifting digital holography utilizing spatial frequency analysis for the correction of the phase-shift error, Optics Letters, vol. 37, No. 2, Jan. 9, 2012.
Jian Fu et al., Fast X-ray Differential Phase Contrast Imaging with One Exposure and without Movements, Scientific Reports, Feb. 4, 2019.
Yongshuai Ge et al., Grating based x-ray differential phase contrast imaging without mechanical phase stepping, Optics Express, vol. 22, No. 12, Jun. 3, 2014.
Chen-Xi Wei et al., Single-shot grating-based x-ray differential phase contrast imaging with a modified analyzer grating, Chinese Physics B, vol. 26, No. 10, Sep. 10, 2017.

* cited by examiner

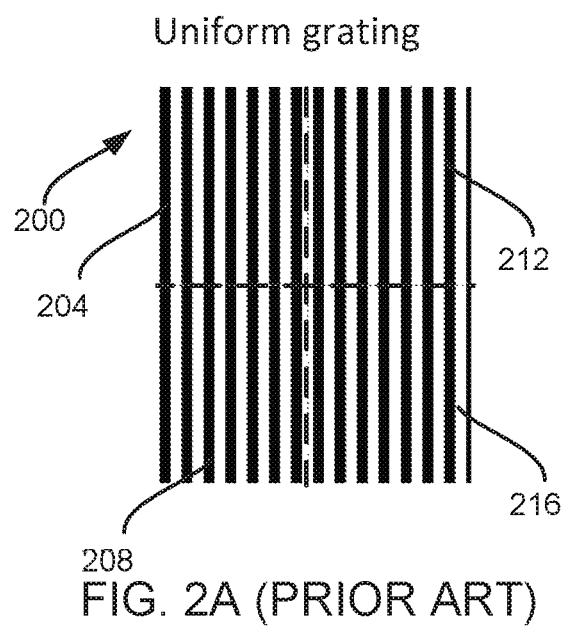
FIG. 2A (PRIOR ART)
FIG. 2B (PRIOR ART)
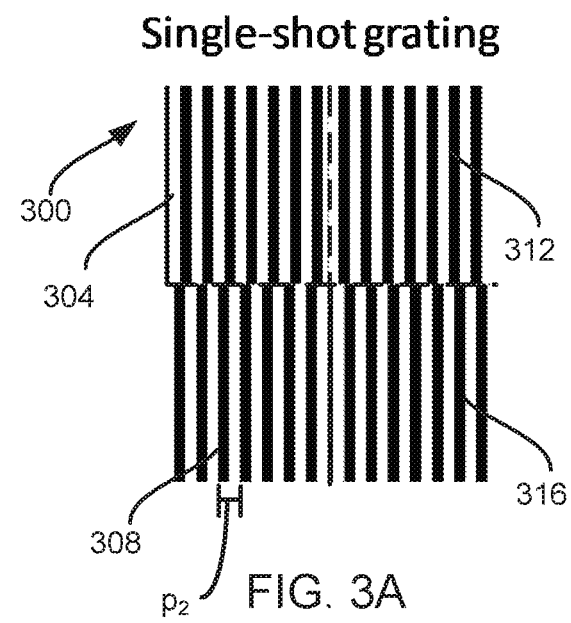
FIG. 3A
FIG. 3B

| 0 | π/2 | 0 | π/2 | 0 | π/2 | 0 | π/2 |
|---|---|---|---|---|---|---|---|
| 3π/2 | π | 3π/2 | π | 3π/2 | π | 3π/2 | π |
| 0 | π/2 | 0 | π/2 | 0 | π/2 | 0 | π/2 |
| 3π/2 | π | 3π/2 | π | 3π/2 | π | 3π/2 | π |
| 0 | π/2 | 0 | π/2 | 0 | π/2 | 0 | π/2 |
| 3π/2 | π | 3π/2 | π | 3π/2 | π | 3π/2 | π |
| 0 | π/2 | 0 | π/2 | 0 | π/2 | 0 | π/2 |
| 3π/2 | π | 3π/2 | π | 3π/2 | π | 3π/2 | π |

400

| 0 | π/2 | 0 | π/2 | 0 | π/2 | 0 | π/2 |
|---|---|---|---|---|---|---|---|
| 3π/2 | π | 3π/2 | π | 3π/2 | π | 3π/2 | π |
| 0 | π/2 | 0 | π/2 | 0 | π/2 | 0 | π/2 |
| 3π/2 | π | 3π/2 | π | 3π/2 | π | 3π/2 | π |
| 0 | π/2 | 0 | π/2 | 0 | π/2 | 0 | π/2 |
| 3π/2 | π | 3π/2 | π | 3π/2 | π | 3π/2 | π |
| 0 | π/2 | 0 | π/2 | 0 | π/2 | 0 | π/2 |
| 3π/2 | π | 3π/2 | π | 3π/2 | π | 3π/2 | π |

FIG. 6A

| 0 | π/2 | 0 | π/2 | 0 | π/2 | 0 | π/2 |
|---|---|---|---|---|---|---|---|
| 3π/2 | π | 3π/2 | π | 3π/2 | π | 3π/2 | π |
| 0 | π/2 | 0 | π/2 | 0 | π/2 | 0 | π/2 |
| 3π/2 | π | 3π/2 | π | 3π/2 | π | 3π/2 | π |
| 0 | π/2 | 0 | π/2 | 0 | π/2 | 0 | π/2 |
| 3π/2 | π | 3π/2 | π | 3π/2 | π | 3π/2 | π |
| 0 | π/2 | 0 | π/2 | 0 | π/2 | 0 | π/2 |
| 3π/2 | π | 3π/2 | π | 3π/2 | π | 3π/2 | π |

FIG. 7A

| | | | |
|---|---|---|---|
| 0 | 12 | 3 | 15 |
| 4 | 8 | 7 | 11 |
| 1 | 13 | 2 | 14 |
| 5 | 9 | 6 | 10 |

FIG. 14

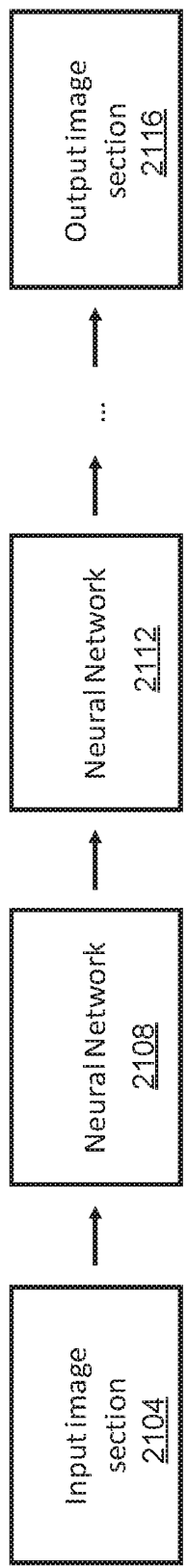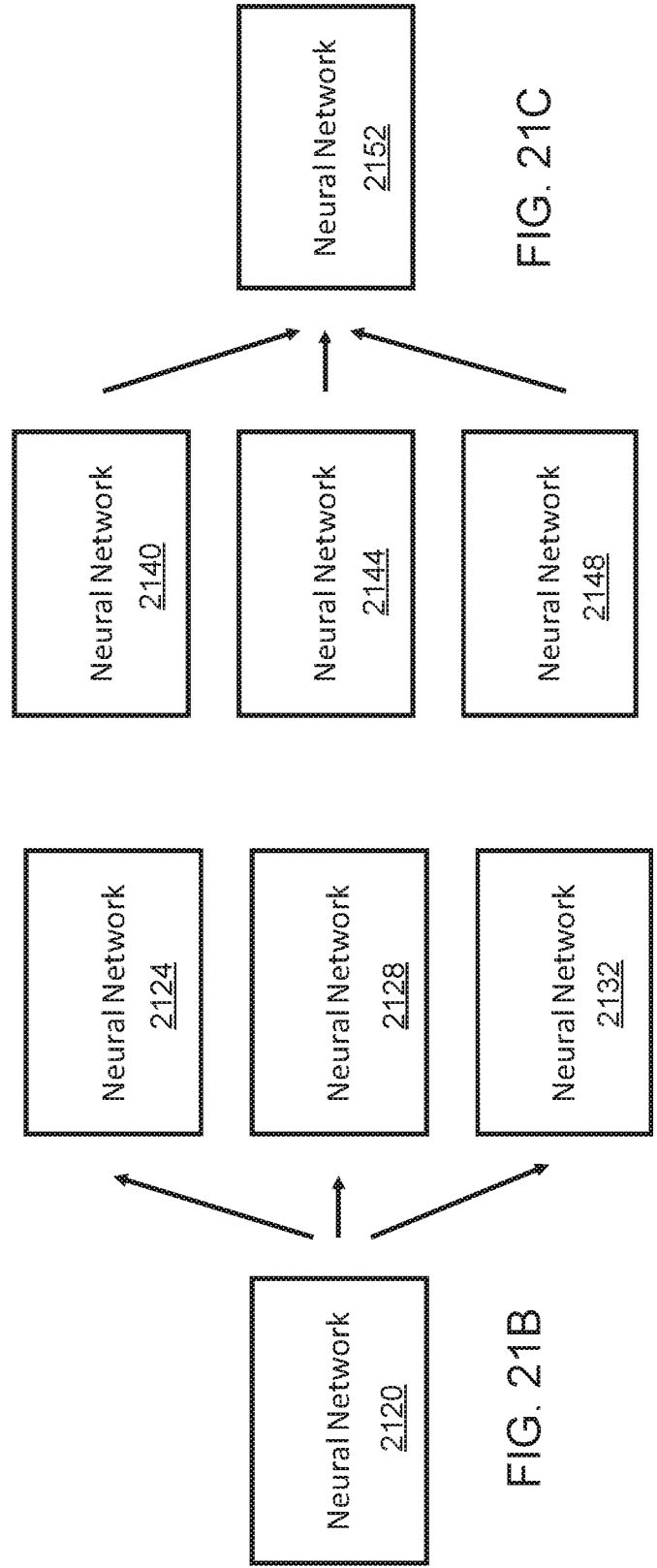
FIG. 21A
FIG. 21B
FIG. 21C

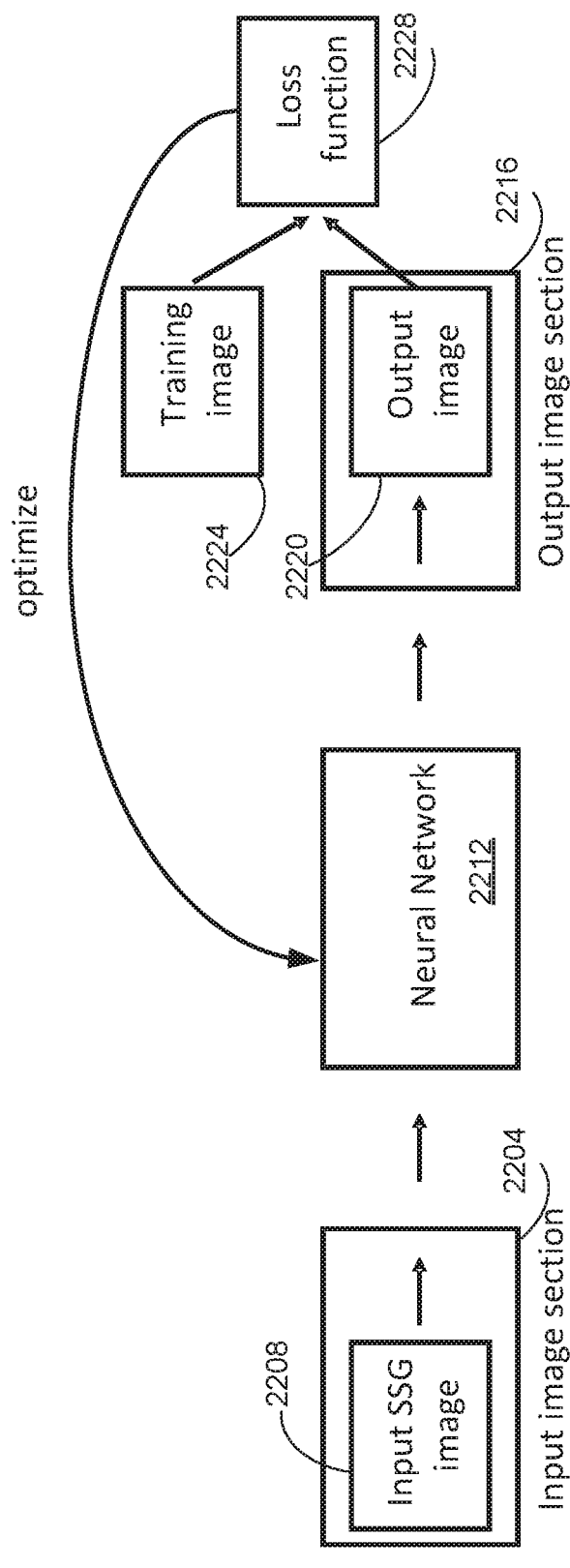
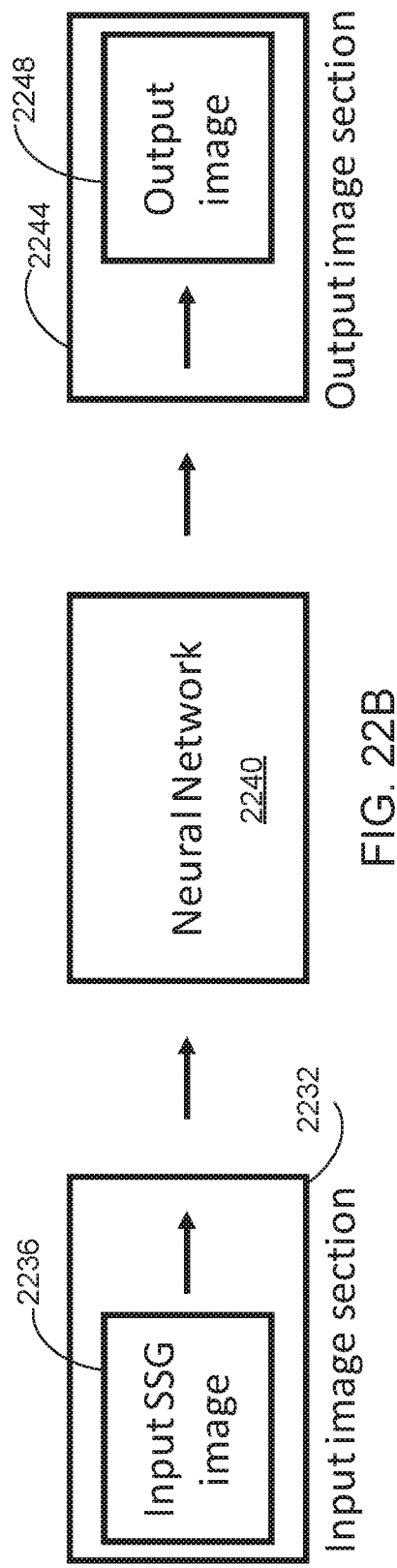
FIG. 22A
FIG. 22B

SINGLE SHOT ANALYZER GRATING FOR DIFFERENTIAL PHASE CONTRAST X-RAY IMAGING AND COMPUTED TOMOGRAPHY

CROSS-REFERENCE TO RELATED APPLICATION

This application claims the benefit of priority of U.S. Application No. 62/897,011, filed Sep. 6, 2019, which is incorporated herein by reference for all purposes.

GOVERNMENT RIGHTS

This invention was made with Government support under contracts HSHQDC-12-C-00002 and HSHQDC-17-C-00053 awarded by the US Department of Homeland Security, Science and Technology Directorate Explosives Division, and HSTS04-17-C-CT7224 awarded by Transportation Security Administration. The Government has certain rights in the invention.

BACKGROUND

This disclosure relates generally to X-ray imaging. More specifically, the disclosure relates to differential phase contrast (DPC) gratings for X-ray imaging.

SUMMARY

In accordance with the invention, an X-ray amplitude analyzer grating adapted for use in an interferometric imaging system, the interferometric imaging system comprising an X-ray source and an X-ray detector with an X-ray fringe plane between the X-ray source and the X-ray detector, wherein an X-ray fringe pattern is formed at the X-ray fringe plane is provided. The X-ray amplitude analyzer grating comprises a plurality of grating pixels across two dimensions of the X-ray amplitude analyzer grating, wherein each grating pixels of the plurality of grating pixels has a different pattern with respect to all adjacent grating pixels to the grating pixel so that all adjacent grating pixels do not have a same pattern as the grating pixel.

In another manifestation of the invention, an X-ray system for imaging an object is provided. An X-ray source is provided. An X-ray detector with a plurality of detector pixels is spaced apart from the X-ray source. A first X-ray grating is between the X-ray source and the X-ray detector. A second X-ray grating is between the first X-ray grating and the X-ray detector, wherein the second X-ray grating has a plurality of grating pixels across two dimensions, wherein a grating pixel has a different pattern with respect to all grating pixels adjacent to the grating pixel.

In another manifestation of the invention, a method for X-ray imaging an object in an X-ray system comprising an X-ray source, an X-ray detector, a first X-ray grating between the X-ray source and the X-ray detector, and a second X-ray grating between the first X-ray grating and the X-ray detector, wherein the second X-ray grating has a plurality of grating pixels across two dimensions, wherein a grating pixel has a different pattern with respect to all grating pixels adjacent to the grating pixel is provided. X-rays from the X-ray source pass through the object, the first X-ray grating, and the second X-ray grating to the X-ray detector in a single shot. X-ray detection data is received from the X-ray detector. The X-ray detection data is used to create an image of the object.

In another manifestation, an X-ray system for imaging an object is provided. An X-ray source is provided. An X-ray detector with a plurality of detector pixels is spaced apart from the X-ray source. A first X-ray grating is between the X-ray source and the X-ray detector. A second X-ray grating is between the first X-ray grating and the X-ray detector, wherein the second X-ray grating has a plurality of grating pixels across two dimensions, wherein a grating pixel has a different pattern with respect to all grating pixels adjacent to the grating pixel in a first dimension and wherein in a second dimension adjacent grating pixels are staggered with respect to the grating pixel.

In another manifestation, a method for X-ray imaging an object in an X-ray system comprising an X-ray source, an X-ray detector, a first X-ray grating between the X-ray source and object, and a second X-ray grating between the first X-ray grating and the X-ray detector, wherein the second X-ray grating has a plurality of grating pixels across at least one dimension, wherein each grating pixel has a different pattern with all grating pixels adjacent to the grating pixel in the at least one dimension is provided. X-rays pass from the X-ray source through the object, the first X-ray grating, and the second X-ray grating to the X-ray detector for a single shot. X-ray detection data is received from the X-ray detector for the single shot. Artificial intelligence is applied to the X-ray detection data for the single shot to create an image of the object.

The invention and objects and features thereof will be more readily apparent from the following detailed description and appended claims when taken with the drawings.

BRIEF DESCRIPTION OF THE DRAWINGS

FIGS. 2A-B illustrate a grating system used in the prior art.

FIG. 3A-B illustrate a grating system used in an embodiment.

FIG. 6A illustrates 2×2 single shot grating (SSG) patterns that are used in an embodiment.

FIG. 7A illustrates 2×2 SSG patterns that are used in another embodiment.

FIG. 14 is a table showing phase shifts for grating pixels for a 4×4 unit cell used in another embodiment.

FIG. 21A shows a neural network model using a plurality of neural network blocks in an embodiment.

FIG. 21B shows a neural network can be fed into a split of three neural network branches in another embodiment.

FIG. 21C shows the outputs of three neural network branches can be merged and fed into a neural network in another embodiment.

FIG. 22A shows a training process in a supervised learning.

FIG. 22B shows utilizing a neural network model to reconstruct SSG images.

DETAILED DESCRIPTION OF ILLUSTRATED EMBODIMENTS

X-ray differential phase contrast (DPC) imaging uses an X-ray imaging system utilizing an X-ray interferometer to detect the changes in X-ray phases when X-rays propagate through objects. X-ray phase contrast imaging techniques can be realized using a synchrotron radiation X-ray source or a relatively weak micro-focused X-ray source. A more popular way is to use a three-grating based X-ray DPC imaging system, which provides a way to make use of more commonly used large spot X-ray source and large pixel-size X-ray detectors for DPC imaging.

Figure 1:
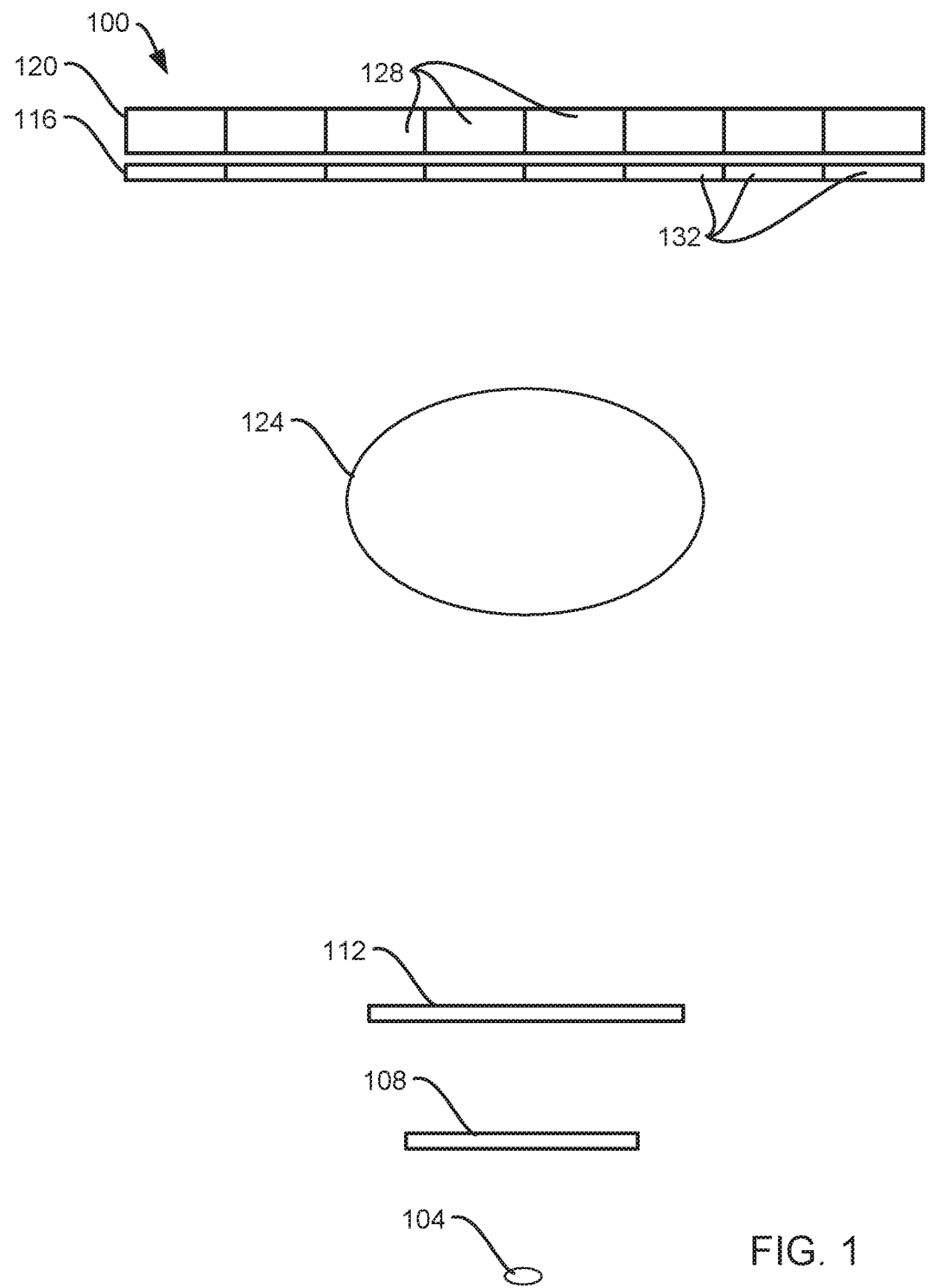
FIG. 1 is a schematic view of an embodiment of an X-ray imaging apparatus used in an embodiment.

FIG. 1 is a schematic view of an embodiment of an X-ray imaging apparatus, such as an X-ray DPC imaging system 100. The X-ray DPC imaging system 100 comprises an X-ray source 104, a first grating 108, a second grating 112, a third grating 116, and an X-ray detector 120. The third grating 116 is an X-ray amplitude analyzer grating. An object 124 to be imaged is placed between the second grating 112 and the third grating 116. The object 124 is a material imaging object. In the same way, the first grating 108, second grating 112, third grating 116, and X-ray detector 120 extend out of the page. In this embodiment, the X-ray detector 120 is an 8×8 pixel array; it can be termed an 8×8 detector. So, a cross-sectional view of the X-ray detector shows 8 pixels 128 of the X-ray detector 120. The third grating 116 is an 8×8 grating pixel array in this embodiment; it can be termed an 8×8 grating. So, a cross-sectional view of the third grating 116 shows 8 grating pixels 132. Each grating pixel 132 of the third grating 116 corresponds to a pixel 128 of the X-ray detector 120. In other embodiments, the object 124 may be placed between the first grating 108 and the second grating 112. In other embodiments, there is no need to have the first grating 108 if the spot size of the X-ray source 104 has a dimension similar to the design of the pitch of the first grating 108.

To have sufficient spatial coherence to form the X-ray interference fringes, the X-ray source 104 usually needs to be smaller than 10 μm (depending on the interferometer design, e.g. X-ray energy and spacing between X-ray source, gratings, and detectors). However, most of the X-ray sources used in commercial computed-tomography (CT) scanners for aviation security and medical imaging have a source spot ranging from a few hundred micrometers to a few millimeters. The first grating 108, the source amplitude grating (G0), with pitch $p_0$, can be used in front of the X-ray source to mask a big extended X-ray source into effectively multiple thin-slit X-ray line sources. The pitch (or period), the constant distance between the centers of the thin slits, can be designed such that the X-ray fringes formed from each of the thin slit sources formed by the first grating 108 overlap completely at the position of the third grating 116. Embodiments with a sufficiently small X-ray source 104 do not need a first grating 108.

Before an object 124 is inserted in the X-ray DPC imaging system 100, a periodic X-ray interference fringe pattern is formed at an X-ray fringe plane right in front of the X-ray detector 120. When an object 124 is inserted in the X-ray beam path, a few things happen, which change the X-ray interference fringe patterns. Some of the X-rays are absorbed by the object 124, which reduces the intensity of the X-ray fringes. Part of the X-ray wavefront is modified by the object 124 because the object's refractive index differs from that of air, which changes the phase of the X-ray wavefront at the X-ray fringes and changes the lateral positions of the fringe pattern locally. Some of the X-rays are scattered off of the object 124, which modifies the X-ray fringe's amplitude. Depending on the X-ray interferometer designs, the pitch of the X-ray fringes in front of the X-ray detector 120 could be on the scale of micrometers. However, pixel sizes of commercially available X-ray detectors usually range from tens of micrometers to a few millimeters. It is not possible to detect the position changes in the X-ray fringe pattern with detectors having such big pixels. To discover the position changes of the X-ray fringe patterns, the third grating 116, analyzer amplitude grating (G2), with a pitch $p_2$, is placed right in front of the X-ray detector 120. The third grating 116 has the same pitch (or period) as the X-ray fringe pitch in front of the X-ray detector 120 and is close enough to the X-ray fringe plane to allow measurement of the X-ray fringe pattern. If all of the bright fringes (where the maximum X-ray intensity is located) are aligned with the open slits of the third grating 116, the X-ray detector 120 would get an integrated "high" signal. On the other hand, if all of the dark fringes (where the minimum X-ray intensity is located) are aligned with the third grating 116 open slits, the detector would get an integrated "low" signal. Conventionally, phase stepping by shifting the third grating 116 laterally by portions of one pitch using a motor will lead to an oscillating series of measurements in each pixel. By fitting the series of measurements with a curve, the X-ray fringe pattern's intensity ($I_0$), amplitude (A), and phase ($\phi$) can be retrieved in each pixel. The intensity, amplitude, and phase are called fringe parameters. The intensity values in all pixels together form the intensity image, and likewise for the amplitude and phase. The intensity image, amplitude image, and phase image together are called three-channel images.

A phase-stepping measurement performed with no object in the beam path is called a reference scan, and a phase-stepping measurement performed with an object in the beam path is called an object scan. By comparing the fringe parameters of the reference scan and the fringe parameters of the object scan, three different X-ray images can be obtained: the absorption contrast image, ABS (equivalent to traditional X-ray images); the differential phase contrast image, DPC; and the dark-field contrast image, DF:

$$ABS = \frac{I_{0,obj}}{I_{0,ref}},$$

$$DPC = \phi_{obj} - \phi_{ref},$$

$$DF = 1 - \frac{A_{obj}/I_{0,obj}}{A_{ref}/I_{0,ref}}.$$

[1]

The absorption contrast image, differential phase contrast image, and dark-field contrast image together are termed three-channel contrast images or three-signature contrast images (distinct from the three-channel images defined above). They can be obtained from a DPC imaging system by phase stepping, as described above, but also from a single-shot (single exposure) image using this invention.

There are multiple ways to design the second grating 112. For example, re-phase shift or π/2-phase shift are the most popular choices, and there are also multiple options of utilizing different orders of Talbot self-images to locate the G2 analyzer gratings. One common solution (π-phase shift G1 with first-order Talbot self-image) among all possible solutions is used to explain the design rules.

One of the line sources, extended in and out of the page, located immediately after the first grating 108 is formed by filtering the original X-ray source 104 with the first grating 108. The first (G0) grating 108 is located at a distance l in front of the second (G1) grating 112, which is a π-phase shift G1 grating (with a pitch of $p_1$). A Talbot self-image of the diffracted X-ray fringes is formed at a distance $$d = \frac{l+d}{l} \frac{p_1^2}{8\lambda}$$

down field of the second grating 112, where d is the distance between the second grating 112 and the third grating 116, and λ is the wavelength of the monochromatic X-ray wavelength used in the design process. The X-ray fringe pitch is equal to $$\frac{l+d}{l} \frac{p_1}{2}.$$

By solving the equation $$d = \frac{l+d}{l} D_1,$$

where $$D_1 = \frac{p_1^2}{8\lambda} D_I = p_I^2/(8\lambda),$$

two geometries may be found which satisfy the imaging condition:

$$l = \frac{s}{2} \pm \sqrt{\frac{s^2}{4} - sD_1}.$$

Here, s=l+d and s is the distance between the first grating 108 and the third grating 116. Therefore, if an imaging system design exists with l<d, another design exists with l>d, offering some flexibility. Finally, when l and d are chosen, a simple geometric relation is used to decide the pitch of the G0 grating by $$p_0 = \frac{l}{d} p_2.$$

The X-ray DPC imaging system's parameters are related by the wavelength (λ) of the X-rays and therefore determined by the energy (E) of the X-rays by $$E = \frac{hc}{\lambda},$$

where h is the Planck constant and c is the speed of light.

In addition to the system's dimensions, the choice of the design energy for the X-ray DPC imaging system is usually informed by the imaging application. The wavelength (λ), and therefore the energy of the X-rays is described for monochromatic X-rays by the previously mentioned equations. Although typical commercially available polychromatic X-ray sources emit a broad spectrum of energies, the monochromatic equations above are still useful for the design of polychromatic X-ray DPC imaging systems. Usually, the design energy (or wavelength) involved in those equations is close to the mean energy (or wavelength) of the X-ray source or the X-rays reaching the X-ray detector. This design energy can be obtained through optimization of the resulting fringe contrast using well-known design principles in the art. For applications focused on relatively small objects or low-absorptive materials such as mammography and dental X-rays, X-rays do need to penetrate the small objects. Relatively low mean X-ray energies, such as less than 40 keV, may be used. On the other hand, for big objects with more absorptive materials, such as luggage scanned by aviation security CT scanners, a much higher mean X-ray energy would be needed, e.g. 90-100 keV.

In most grating-based X-ray differential phase contrast (DPC) imaging systems, the image information stored in the DPC fringes can be retrieved by using an analyzer grating (G2 grating) having the same period as the DPC fringes right in front the detector panel. The intensity measured by each pixel of the detector panel is a sum over the X-ray photons which pass through the G2 grating over that pixel. By taking repeated images while incrementally moving the G2 grating along the direction of the grating vector, a series of detected intensities can be obtained in each pixel, varying sinusoidally with G2 displacement. The intensity in each pixel on exposure i can be parameterized with the following equation:

$$I^i = I_0 + A\cos\left(\frac{2\pi x_{G2}^i}{p_2} + \phi\right) \quad [2]$$

which describes the dependence of the measured signal I on the lateral displacement $x_{G2}$ of the G2 grating. $I_0$, A, and $\phi$ are the parameters that can be fitted to recover the intensity, amplitude, and phase information from the measured intensities $I^i$. This phase-stepping method is said to be performed temporally because signals of different "phase steps" are measured at different times.

In most present-day radiography, X-ray images are single exposures which are interpreted in isolation. Examples include chest X-rays, dental X-rays, and X-ray imaging for bone inspection. Taking a series of X-ray images of the same object in the same orientation, as necessary for conventional DPC X-ray imaging, could result in motion artifacts if the object is not absolutely still. For instance, when imaging human patients, breathing and incidental motion create motion artifacts. Therefore, it is advantageous in some applications to obtain X-ray DPC images with a single exposure. Instead of acquiring a series of X-ray images of different G2 grating phase shifts temporally at different time steps, the phase shift information can also be recorded spatially at different locations of the X-ray detector. In the prior art, the G2 grating was designed with a plurality of columns of X-ray grating patterns with the grating pattern of each column having a different phase shift compared to its adjacent grating columns Therefore, the phase information needed to reconstruct the three-channel images, $I_0$, A, and $\phi$ can be obtained from different pixels in the same rows of a single exposure. The spatial changes of the G2 X-ray grating pattern in one dimension are analogous to moving a uniformly patterned G2 X-ray grating in one dimension. Because the G2 pattern is varied in one dimension, this single-shot grating can be termed a 1D single shot grating (1D SSG). Such schemes trade temporal resolution for spatial resolution. From a general mathematical point of view, at least three measurement data points are needed to fit Equation 2 and obtain, $I_0$, A, and $\phi$. More measurement data points would be even better for reducing noise and systematic phase error. However, the more pixels are used for recovery of local fringe parameters, the more resolution is lost. Furthermore, the true fringe parameters vary spatially because they depend on the shape of the object. The expected spatial variation of fringe parameters is difficult to disambiguate from the spatial modulation caused by a single-shot grating. This ambiguity can lead to large errors in the three-channel image reconstruction. We will describe this in more detail in the later paragraphs.

In this invention, we employ a new 2D single-shot G2 X-ray grating (2D SSG). The 2D SSG is analogous to the Bayer filter common in digital cameras. By distributing the different phase shifts of the grating in two dimensions instead of one, spatial resolution can be improved. Furthermore, because the fringe parameters tend to vary smoothly in the image plane, the recovery of fringe parameters at a point will be most accurate by drawing data from a compact neighborhood of pixels in two dimensions, instead of reaching a long distance along its row of pixels. We will also cover resolution recovery methods in some embodiments using our invention.

In this invention, the G2 grating is partitioned into a regular grid of rectangular regions in both rows and columns. These regions are called grating pixels. Each grating pixel corresponds to one or more pixels of the detector. In some embodiments, grating pixels are arranged such that all X-rays from the source passing through a grating pixel land in its corresponding detector pixels; and all X-rays from the source landing in a detector pixel pass through its corresponding grating pixel. The detector pixels corresponding to one grating pixel are said to belong to the grating pixel. In some embodiments, the G2 grating is curved cylindrically or spherically to better match the X-ray wavefronts. Therefore, if the detector is flat and the G2 grating is curved, then the grating pixels will have nonuniform sizes. In some embodiments the G2 grating is flat. If the grating is flat and the G2 grating is flat, then the grating pixels will be rectangular and of the same dimensions.

In some embodiments, the grating pixels are arranged in a regular Cartesian grid (square lattice), such that each grating pixel shares edges with up to four other grating pixels. In some embodiments, the grating pixels are arranged in a hexagonal lattice by offsetting every second row (or every second column) of grating pixels by a distance equal to half the size of a grating pixel in that direction, such that each grating pixel shares edges with up to six other grating pixels. Each grating pixel in a hexagonal lattice must contain at least two detector pixels. In a hexagonal lattice, some grating pixels at the edge of the grating will be truncated to half their usual size, due to the offsetting. Other embodiments may tesselate the grating with other patterns of grating pixels.

In some embodiments, the detector will use "binning" to reduce the effective resolution of the detector and decrease noise. Binning groups several pixels together and sums their values, creating a larger effective pixel size. A group of pixels binned together is called a binned pixel. Each binned pixel belongs to only one grating pixel, and the same number of binned pixels belongs to each grating pixel. In some embodiments, one binned pixel belongs to each grating pixel. In other embodiments, several binned pixels belong to each grating pixel.

FIG. 2A shows a G2 grating 200 with uniform grating pixels used in the prior art. In this example, the G2 grating 200 is divided into four grating pixels: a first grating pixel 204, a second grating pixel 208, a third grating pixel 212, and a fourth grating pixel 216. FIG. 2B is a table indicating the phase difference of each grating pixel from the first grating pixel 204 used in the prior art. FIG. 2B shows that all grating pixels are in phase. In such a device, measurements are taken over time and the entire grating is displaced incrementally over time in order to obtain intensity, differential phase, and amplitude images.

A conventional X-ray grating is a planar-like structure with a space-varying repeating pattern of properties such as thickness. In the short-wavelength limit often pertinent for X-ray optics, a grating's action on an optical wavefront can be described by a pupil function P(x, y) which multiplies the complex amplitude of incident waves. For amplitude gratings, the most important aspect of the pupil function is its modulus $|P(x, y)| \in [0,1]$, where $|P|=1$ is fully transparent and $|P|=0$ is fully opaque. Because gratings are often periodic, a common idealized model for gratings makes use of a phase function f(x, y), and defines the pupil function as a periodic function of the phase. An idealized binary grating could be defined by $$f(x, y) = \frac{2\pi x}{p_G} \quad [3]$$

-continued $$P(x, y) = \begin{cases} 1, \cos f(x, y) > 0 \\ 0, \cos f(x, y) < 0 \end{cases}$$

which models a grating of slits parallel to the y direction, alternating opaque and transparent in the x direction, with a pitch (or period) $p_G$ equal to the width of one opaque and one transparent region, and a duty cycle $$F = \frac{1}{2}.$$

Another uniform grating can be defined by the affine phase function $f = g_x x + g_y y + \psi_G$ where $(g_x, g_y)$ is called the grating vector. The slits of the grating are perpendicular to the grating vector, and the grating's pitch is $$p_G = \frac{2\pi}{\|g\|}.$$

The constant $\psi_G$ is the phase shift of the grating. It effects a uniform shift of the grating parallel to the grating vector by a distance $$-\frac{p_G}{2\pi}\psi_G.$$

A non-affine phase function will give rise to a non-uniform grating. Much of this disclosure concerns non-uniform gratings. For instance, if the plane is partitioned into pixels $P_1, P_2, \ldots$ and so on, a grating phase function may be defined by $$f = \frac{2\pi x}{p_G} + \psi_{G,i}, x \in P_i \quad [4]$$

which can for instance describe the grating of FIG. 3A. Piecewise-affine phase functions may also have a different grating vector in each pixel. Piecewise non-affine gratings include piecewise chirped gratings, where the grating pitch slowly changes inside each pixel.

This invention describes non-uniform gratings where each grating pixel is different than most of its neighbors. Two grating pixels are different if there is a change in the grating pattern at the edge they share, which would not be expected in the interior of a grating pixel. In some embodiments, two grating pixels are different if they are individually described by an affine grating phase function, but cannot be together defined with the same affine grating phase function (e.g. because each pixel has its own grating phase shift or its own grating vector). In other embodiments, two grating pixels are different if they are each described well by a smooth grating phase function but their grating phase functions do not meet smoothly at the edge between the two grating pixels.

Single-Shot Image Analysis

A single-shot method replaces temporally-coded phase steps with spatially-coded phase steps. Instead of displacing the G2 grating over time to obtain a sinusoidal curve as just described, a single-shot method uses a 2D mosaic of grating pixels wherein each grating pixel's phase $\psi_G$ is shifted by a designed phase step compared to a first grating pixel. Therefore, the data measured at different grating phase steps are spatially located in different pixels instead of different points in time. This G2 grating is called a single-shot grating (SSG). The idea of using an SSG is to use a spatially modulated phase-step pattern to recover the DPC fringe parameters from only a single exposure. If the intensity and phase of the X-ray interference fringes vary slowly, an embodiment is able to obtain a very similar sinusoidal curve to that obtained using the temporal phase stepping method.

FIG. 3A shows a G2 grating 300 with varying grating pixels. In this example, the G2 grating 200 is divided into four grating pixels forming a 2×2 unit cell of a first grating pixel 304, a second grating pixel 308, a third grating pixel 312, and a fourth grating pixel 316. FIG. 3B is a table indicating the phase difference of each grating pixel from the first grating pixel 304 so that the first grating pixel 304 has a pattern that is shifted from all adjacent grating pixels. FIG. 3B shows that the second grating pixel 308 and the third grating pixel 312 have a phase difference of $\pm\pi/2$ from the first grating pixel 304 and that the fourth grating pixel 316 has a phase difference of $\pi$ from the first grating pixel 304. The phase difference of all of the adjacent grating pixels from the first grating pixel 304 causes all of the adjacent grating pixels to have a different pattern with respect to the first grating pixel 304. So, all of the adjacent grating pixels have a shifted phase from each other. In this embodiment, the detector pixels are binned within each grating pixel.

Figure 4:
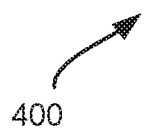
FIG. 4 illustrates an expanded pattern for a single shot grating used in an embodiment.

One way to design an SSG grating is to define a unit cell of several grating pixels with distinct grating phases and tile it in the plane. For example, an 8 pixel×8 pixel G2 grating may be assembled by tiling the unit cell shown in FIG. 3A and FIG. 3B in a 4×4 array of unit cells, forming the single shot grating pattern 400, as shown in FIG. 4.

Reconstruction Algorithms

An SSG image is an image measured from a single exposure using an SSG G2 grating. Because the phase steps (Equation 2) are distributed across many pixels, SSG images must be decoded to obtain the intensity ($I_0$), differential phase ($\phi$), and amplitude (A) images. This decoding task is essential for making use of single shot grating hardware. The fringe parameters vary in the image plane, due to the shapes of objects in the image. This brings ambiguity into the determination of fringe parameters because the contrast of a pixel value with its neighbors cannot be attributed alone to the phase of its G2 grating. We present several example reconstruction algorithms to calculate fringe parameters and recover the resolution sacrificed by the single shot scheme. Three types of algorithms are presented here: simple curve fitting, spatially varying curve fitting, and artificial neural network reconstruction. The simple curve fitting methods approximate the phase stepping curve at a point by gathering data from a neighborhood of nearby grating pixels (a "superpixel") and then perform curve fitting just like conventional temporal phase-stepping methods. This reduces resolution to the size of each neighborhood, but some resolution can be recovered by additional image processing such as interpolation. Such methods may also perform resolution recovery before curve fitting or separate the SSG image into oscillating and non-oscillating parts and build up more complicated algorithms Spatially varying curve fitting begins with a model for space-varying fringes, making use of space-varying polynomials or other building blocks. The SSG image data are treated as samples from the model and minimization or other methods are used to infer the model parameters and reconstruct the entire fringe pattern. Artificial neural network models learn an empirical relation between SSG images and intensity, differential phase, and amplitude; or even an end-to-end processing of object and reference images together to yield the ABS, DPC, and DF images. These models may also be trained to make image improvements such as resolution enhancement, denoising, and removal of optical artifacts.

The intensity, differential phase, and amplitude images decoded from a single exposure may be referred to individually as "processed images" in the following. Together, these three images may be referred to as the "three-channel images." In general, the size (number of pixels) and resolution of a processed image need not be the same as the size and resolution of the SSG image. This is because spatially encoding the grating phase steps sacrifices image resolution: at least three SSG pixels are required to calculate one triple of intensity, differential phase, and amplitude values.

Figure 5A:
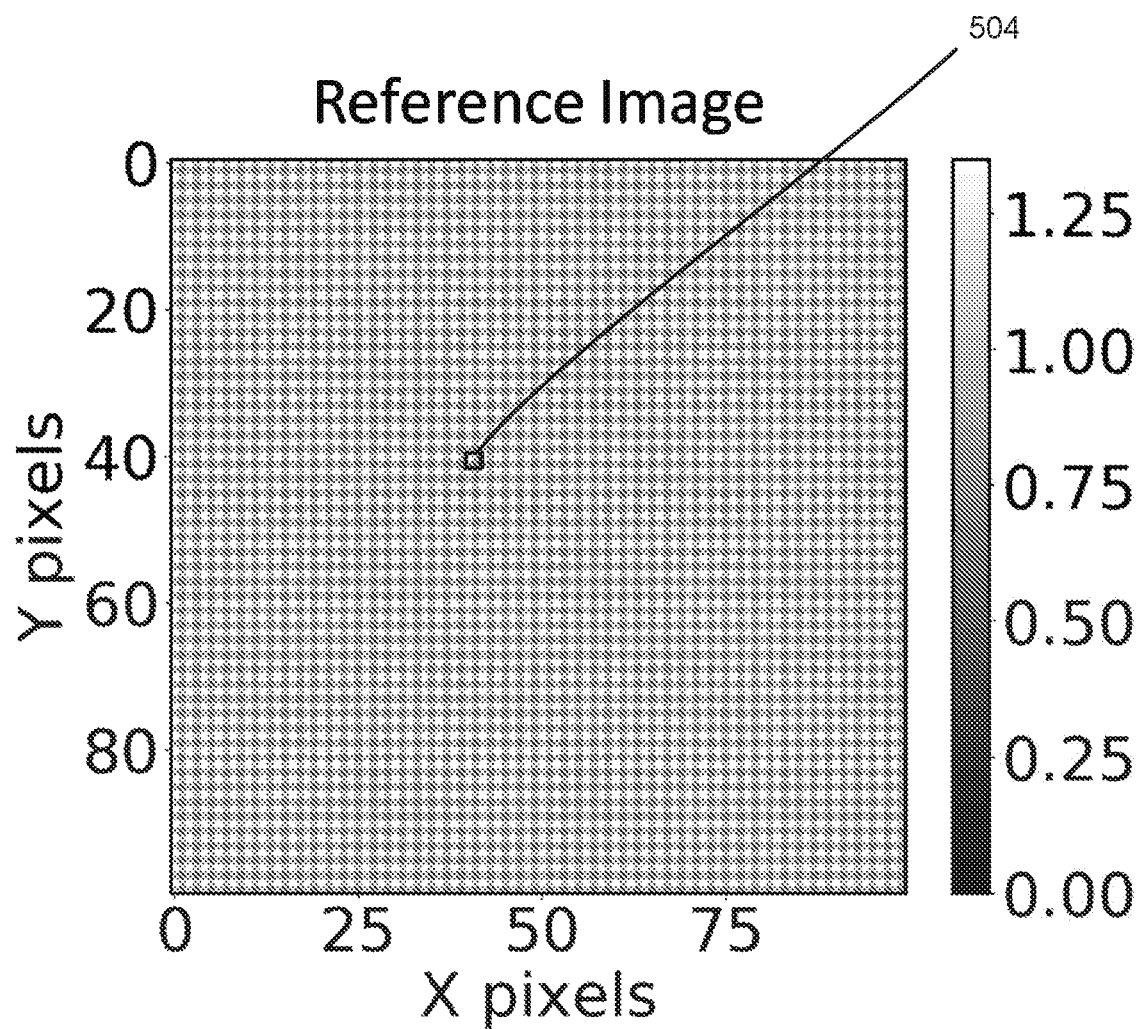
FIG. 5A shows a reference image before an object is placed for imaging.
Figure 5B:
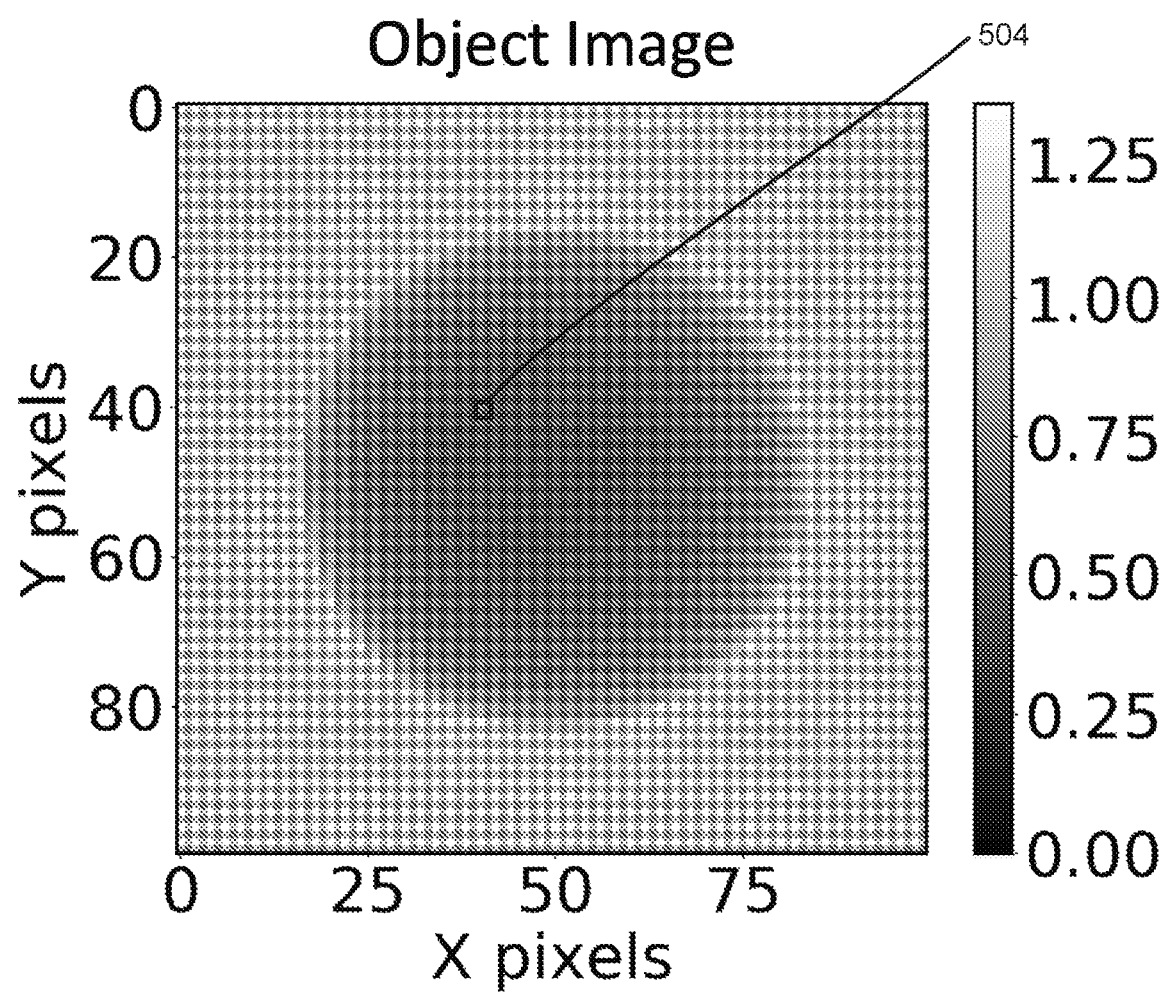
FIG. 5B shows an X-ray image filtered with a single-shot grating of a sphere using an embodiment.
Figure 5C:
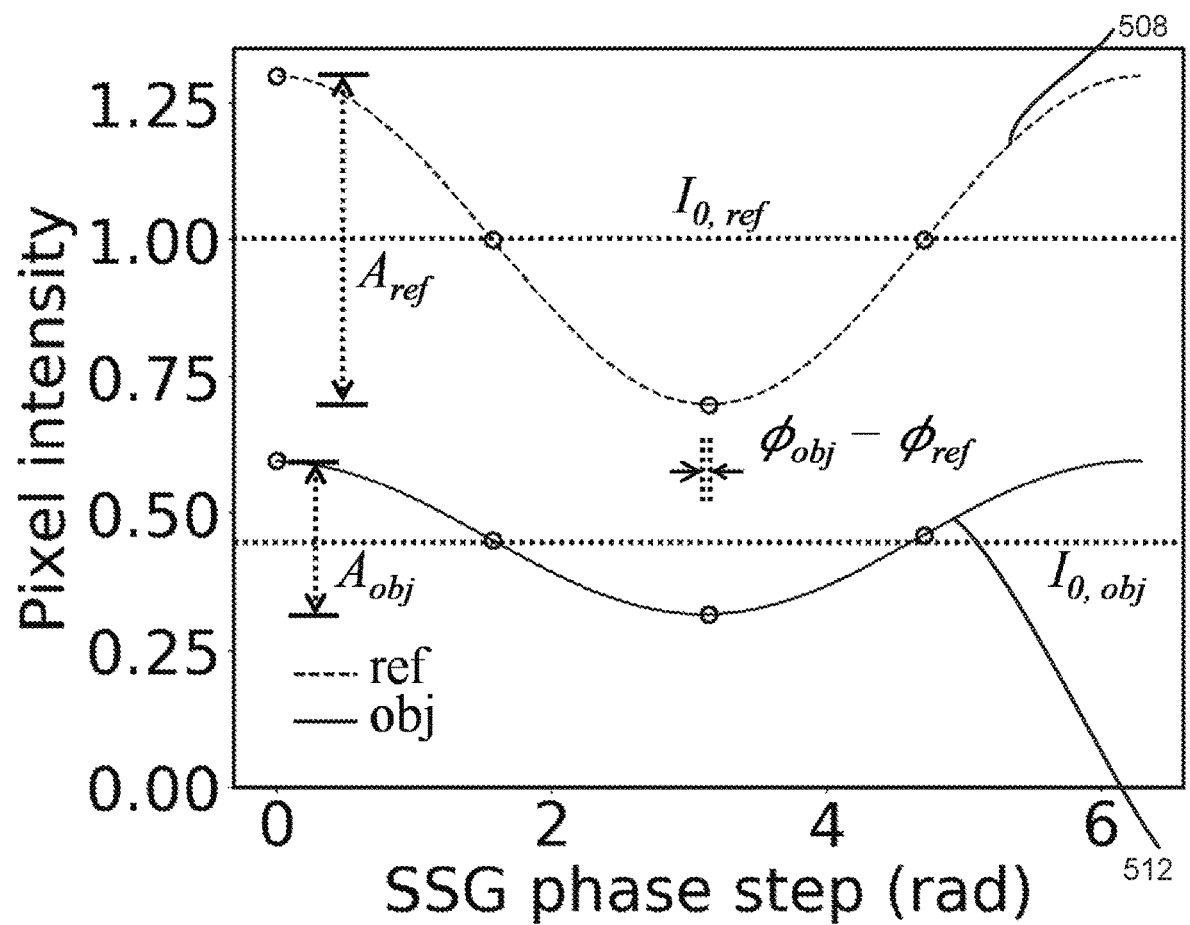
FIG. 5C are graphs of data from a system used in an embodiment.

In some of the methods used in embodiments, the pixels of the SSG image belong to one or more "superpixels." A superpixel is a set of image pixels. In some embodiments, the pixels of the superpixels are contiguous. Superpixels may be the same size as a unit cell of the G2 grating; in some of the methods used in embodiments, the data measured in pixels of a single superpixel can be analyzed together to yield one intensity value, one differential phase value, and one amplitude value, assigned to the entire superpixel. In a method used to recover fringe parameters from a superpixel, the data measured in pixels of the superpixel are sorted in ascending order of the grating pixel phase and interpreted as a phase-stepping curve like Equation 2, and the fringe parameters are retrieved by curve fitting. Sorting the data within one superpixel in ascending order of grating pixel phase can be termed "unrolling." FIG. 5A shows a reference SSG image from a reference shot, i.e. an exposure taken with no object in the beam path in a single shot. FIG. 5B shows an object SSG image, i.e. an exposure taken with an object in the beam path. The square boxes 504 on the reference image in FIG. 5A and on the object image in FIG. 5B enclose 2×2 pixel superpixels at the same location. These data are unrolled into two four-point phase stepping curves, as shown in FIG. 5C; one comes from the reference image and one comes from the object image. Each phase stepping curve can be fitted with a sinusoidal curve according to Equation 2, and fringe parameters recovered. Fitting the data from the superpixel of the reference image yields $I_{0,ref}$, $\phi_{ref}$, and $A_{ref}$. Fitting the data from the superpixel of the object image yields $I_{0,obj}$, $\phi_{obj}$, and $A_{obj}$. Three-channel contrast values can be calculated for this superpixel identically to the case of phase-stepping (Equation 2).

In an embodiment, the SSG image is measured using a 2×2 SSG unit cell as shown in FIG. 6A, and the fitted parameters $I_0$, $\phi$, and A are obtained by Equation 2 followed by retrieving the three-channel contrast images according to Equation 1. This method reduces the image resolution because only three fitted parameters are recovered from each superpixel regardless of the number of grating pixels. The resolution is reduced by 2× in this example because the unit cell is 2×2 pixels.

Figure 6B:
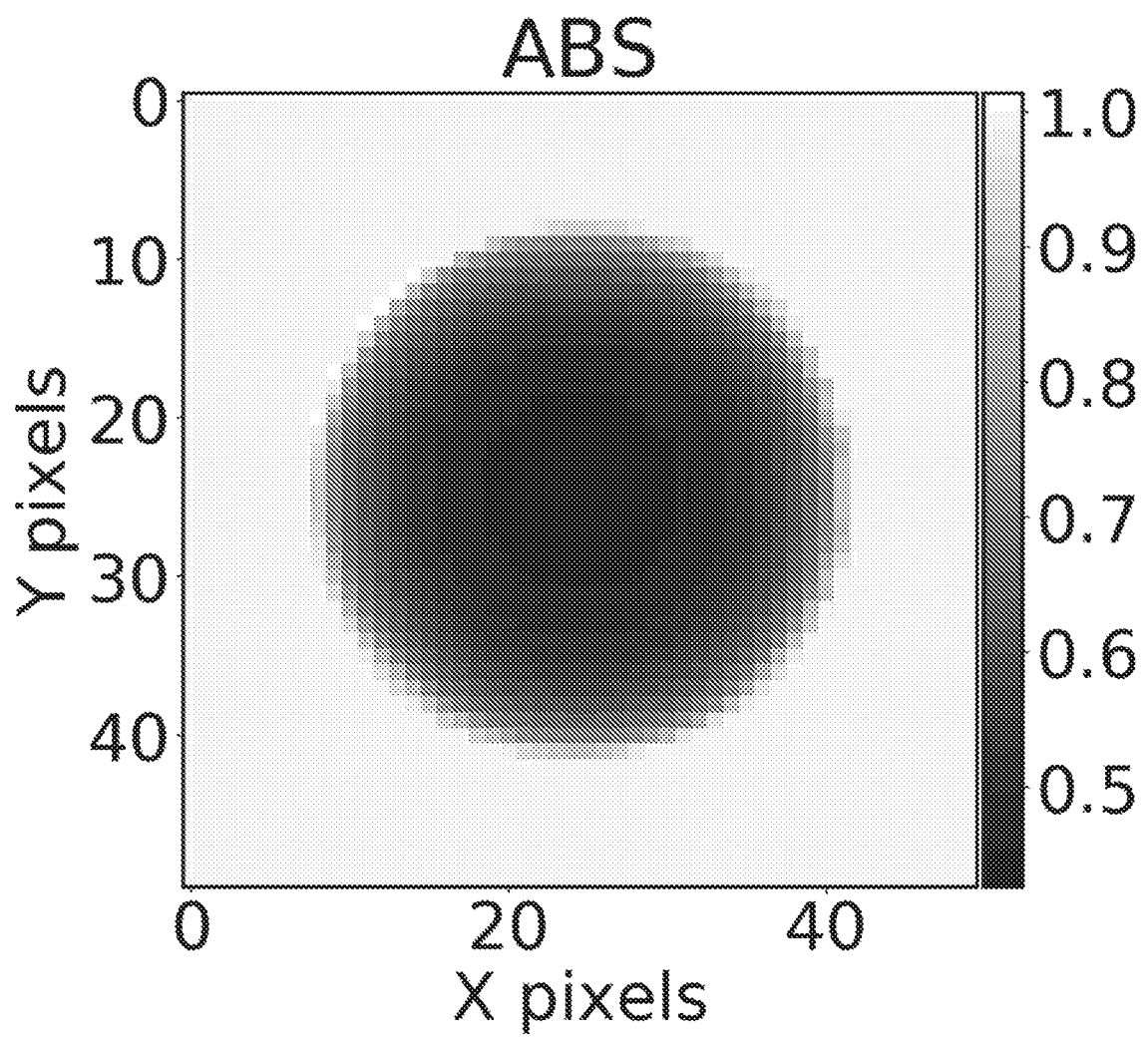
FIGS. 6B-D shows results from the embodiment of FIG. 6A.
Figure 6C:
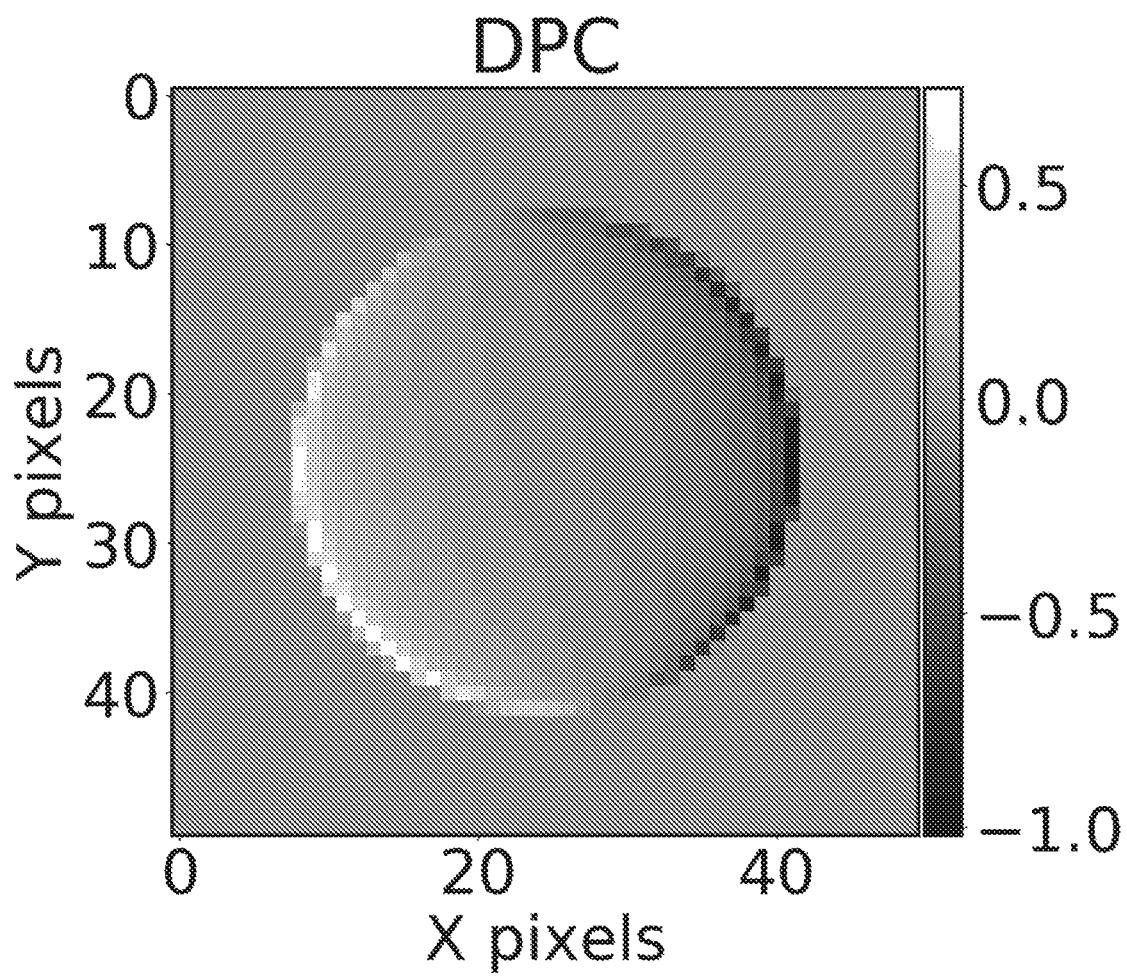
Figure 6D:
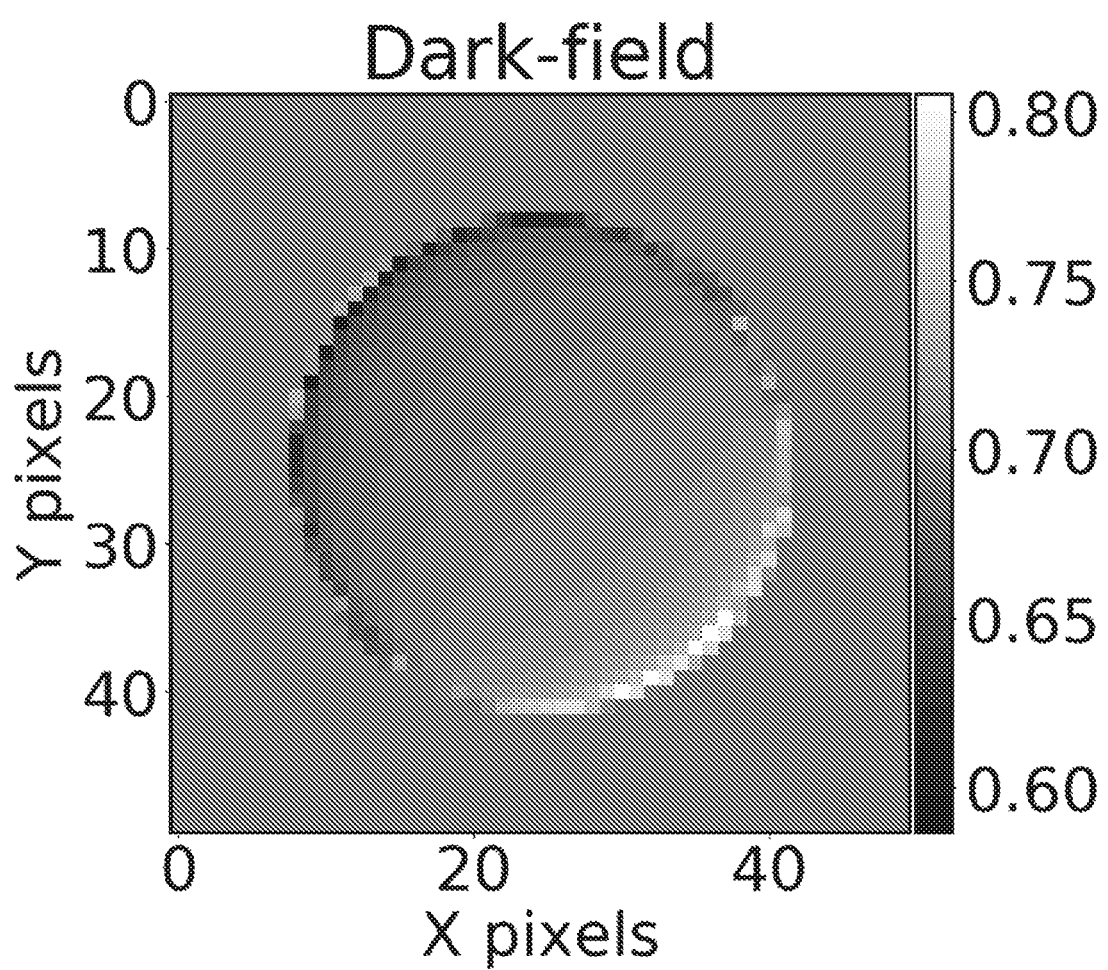

Intensity, amplitude, and differential phase fitted in superpixels may be combined to create three-channel images with the same or different size and resolution as the SSG image. In an embodiment, the SSG image is divided into non-overlapping superpixels as shown in FIG. 6A. Here, a first superpixel 604 comprises pixel (1,1), pixel (1,2), pixel (2,1), and pixel (2,2). A second superpixel 608 is a stride of two pixels to the right of the first superpixel 604, a third superpixel 612 is a stride of two pixels below the first superpixel 604, and a fourth superpixel 616 is a stride of two pixels to the right and two pixels below the first superpixel 604. Three-channel images can be assembled by concatenating the fitted intensity, amplitude, and differential phase from the superpixels. For example, the 8×8 SSG image in FIG. 6A is partitioned into 4×4 superpixels, so the three-channel images are each 4×4 pixels. The resolution is reduced by 2× in this example because the superpixels are 2×2 detector pixels across. In FIG. 6A, the non-overlapping superpixels 604, 608, 612, 616 all correspond to the same SSG unit cell, so the grating pixel phase at pixel coordinates (i, j) relative to the top left pixel of superpixel 604 is the same as the grating pixel phase at coordinates (i, j) relative to the top left pixel of superpixel 608, and so on. Because the four grating pixel phases of each superpixel are distinct, each superpixel's data can be unrolled and fringe parameters obtained by curve fitting. Applying this method to the 100×100 pixel SSG images of FIG. 5A and FIG. 5B, and calculating the contrast images, yields the 50×50 three-channel contrast images of FIG. 6B-D.

Resolution Recovery

With additional operations, either three-channel images or three-channel contrast images can be restored to resolution and size similar to the SSG image. For instance, an SSG image of size 2M×2N is first divided into M×N superpixels each of size 2×2. The three-channel images are obtained, each with size M×N. For each processed image of size M×N, a high-resolution processed image of size (2M−1)×(2N−1) can be created by local operations. Pixels $h_{i,j}$ of the high-resolution processed image will be called high-resolution pixels and pixels $l_{i,j}$ of the original processed image will be called low-resolution pixels. Each high-resolution pixel is calculated as a function of one, two, or four low-resolution pixels, depending on whether its row and column indices are even or odd. For low-resolution pixel coordinates (m, n)

$$h_{2m-1,\ 2n-1} = l_{m,\ n} \quad\quad m \in [1,\ M],\ n \in [1,\ N]$$
$$h_{2m-1,\ 2n} = f_1[l_{m,\ n},\ l_{m,\ n+1}] \quad m \in [1,\ M],\ n \in [1,\ N-1] \quad [5]$$
$$h_{2m,\ 2n-1} = f_2[l_{m,\ n},\ l_{m+1,\ n}] \quad m \in [1,\ M-1],\ n \in [1,\ N]$$
$$h_{2m,\ 2n} = f_3[l_{m,\ n},\ l_{m+1,\ n},\ l_{m,\ n+1},\ l_{m+1,\ n+1}] \quad m \in [1,\ M-1],\ n \in [1,\ N-1]$$

where $f_1$, $f_2$ and $f_3$ could be the mean function or the median function. For instance, the 8×8 SSG image of FIG. 6A can be analyzed to yield 4×4 low-resolution processed images with pixels $l_{i,j}$, and those can be further processed to yield 7×7 high-resolution processed images with pixels $h_{i,j}$. Using the median function, for example, the high-resolution corner pixel $h_{1,1}$ is given the value from the first superpixel 604; the high-resolution edge pixel $h_{1,2}$ is given the median of values from the first superpixel 604 and the second superpixel 608; the high-resolution edge pixel $h_{2,1}$ is given the median of values from the first superpixel 604 and the third superpixel 612; and the high-resolution interior pixel $h_{2,2}$ is given the median of values from the first four superpixels 604, 608, 612, 616. Other methods can also be applied to calculate three-channel contrast images of similar size and resolution to the SSG image, in order to reduce noise or preserve sharp edges.

Figure 7B:
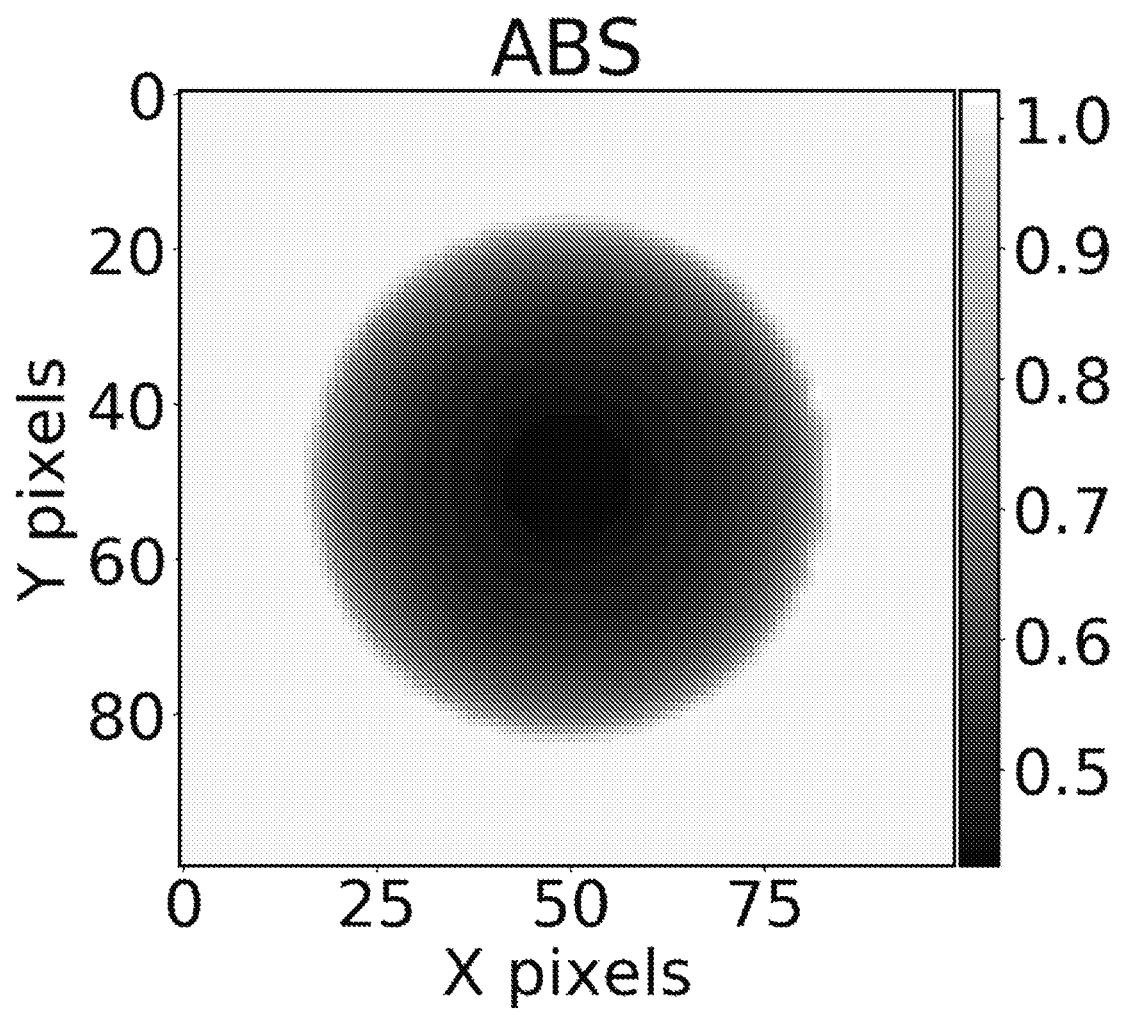
FIGS. 7B-D shows results from the embodiment of FIG. 7A.
Figure 7C:
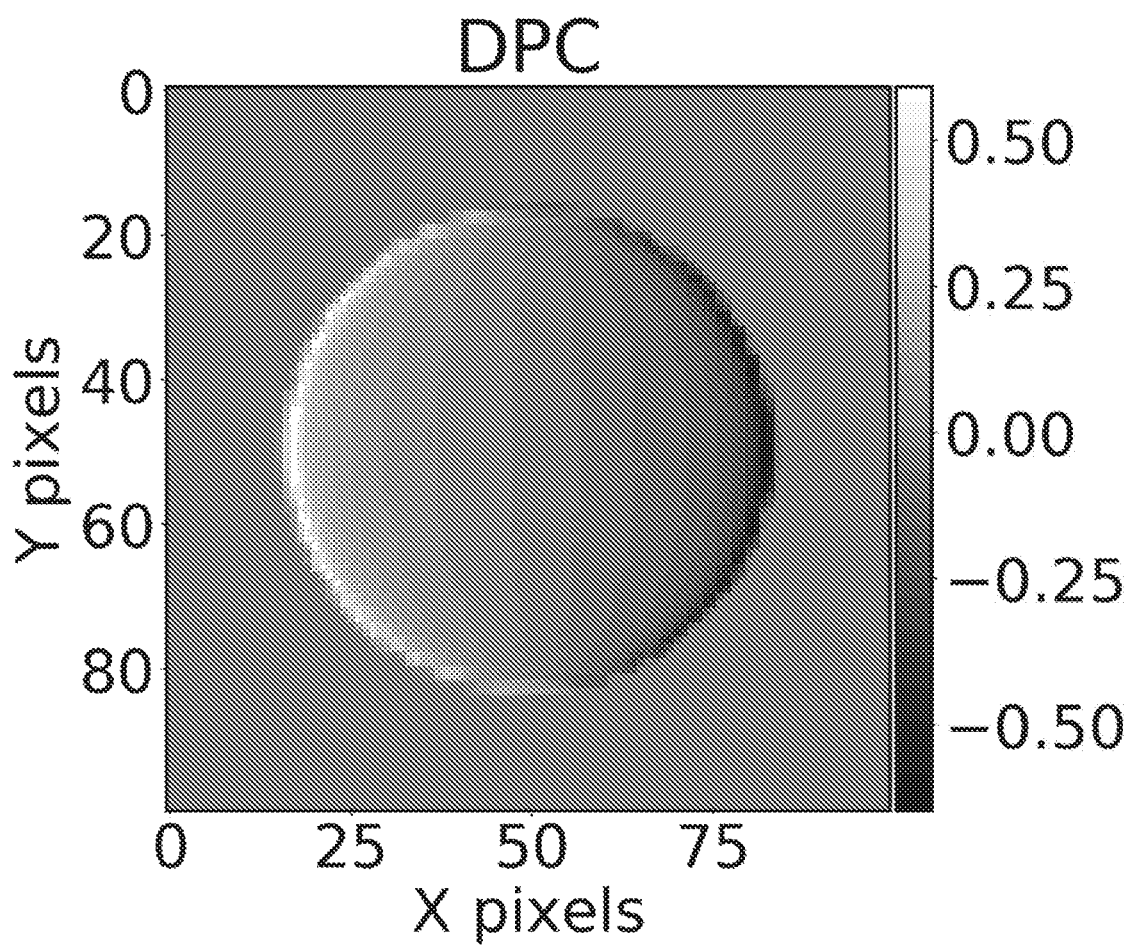
Figure 7D:
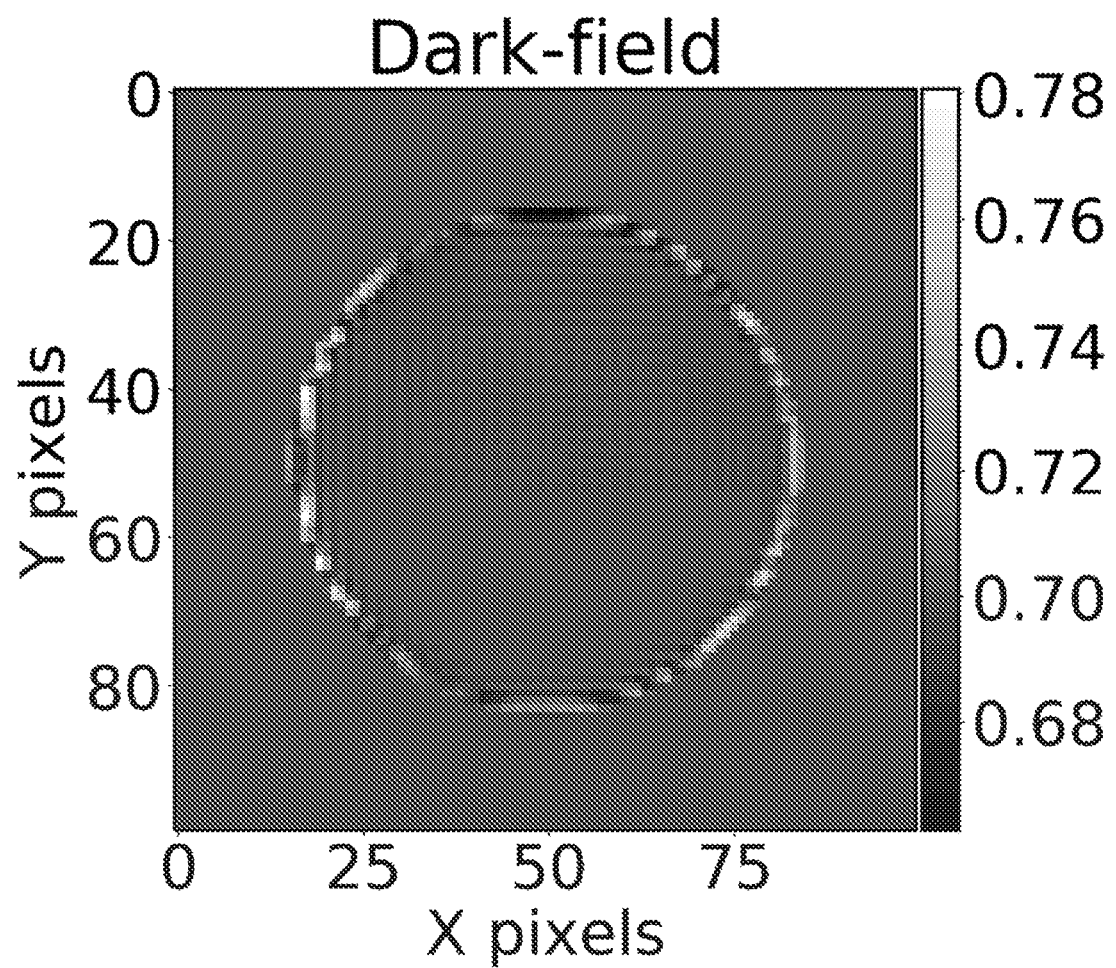

Partially overlapping superpixels may also be defined, each of which has non-repeated grating pixel phases, but the order of the phases need not be identical in each superpixel. FIG. 7A shows 2×2 superpixels separated by a stride of one grating pixel in the x direction and one grating pixel in the y direction. In this embodiment, adjacent superpixels will overlap each other. The first 2×2 superpixel 704 comprises pixel (1,1), pixel (1,2), pixel (2,1), and pixel (2,2). The second 2×2 superpixel 708 comprises pixel (1,2), pixel (1,3), pixel (2,2), and pixel (2,3). The third 2×2 superpixel 712 comprises pixel (2,1), pixel (2,2), pixel (3,1), and pixel (3,2). The fourth 2×2 superpixel 716 comprises pixel (2,2), pixel (2,3), pixel (3,2), and pixel (3,3). Pixels of an SSG image of size 2M×2N are assigned to (2M −1)×(2N−1) overlapping superpixels of size 2×2. Corner pixels of the SSG image only belong to one superpixel, edge pixels of the SSG image belong to two superpixels, and interior pixels of the SSG image belong to four superpixels. A high-resolution processed image of size 2M×2N may be calculated from the SSG image by assigning to each high-resolution pixel the mean or median of values from its enclosing superpixels. For example, with reference to FIG. 7A, processed pixel (1,1) is assigned the value of the first superpixel 704, processed pixel (1,2) is assigned the mean or median of the first superpixel 704 and the second superpixel 708, processed pixel (2,1) is assigned the mean or median of the first superpixel 704 and the third superpixel 712, and processed pixel (2,2) is assigned the mean or median of superpixels 704, 708, 712, and 716. FIGS. 7B-D are three-channel contrast images obtained in this fashion from low-resolution three-channel contrast images FIGS. 6B-D using median filtering. Other methods can also be applied to calculate three-channel images of the same size and resolution as the SSG image, in order to reduce noise or preserve sharp edges.

The $I_0$ values fitted with Equation 2 are essentially the average intensities over entire superpixels. Averaging reduces the image resolution. In another embodiment, the fringe intensity in each pixel can be recovered by demodulating the measured intensity from the SSG. First, fitted three-signature values are obtained in superpixels at a stride of (1,1) in both the x and y directions as shown in FIG. 7A. Within one superpixel, the demodulated intensity in each of its pixels can be obtained using the equation $$I_{0,demod} = I_{signal} - A_{fit} \cos\left(\frac{2\pi x_{G2}}{p_2} + \phi_{fit}\right). \quad [6]$$

Figure 8:
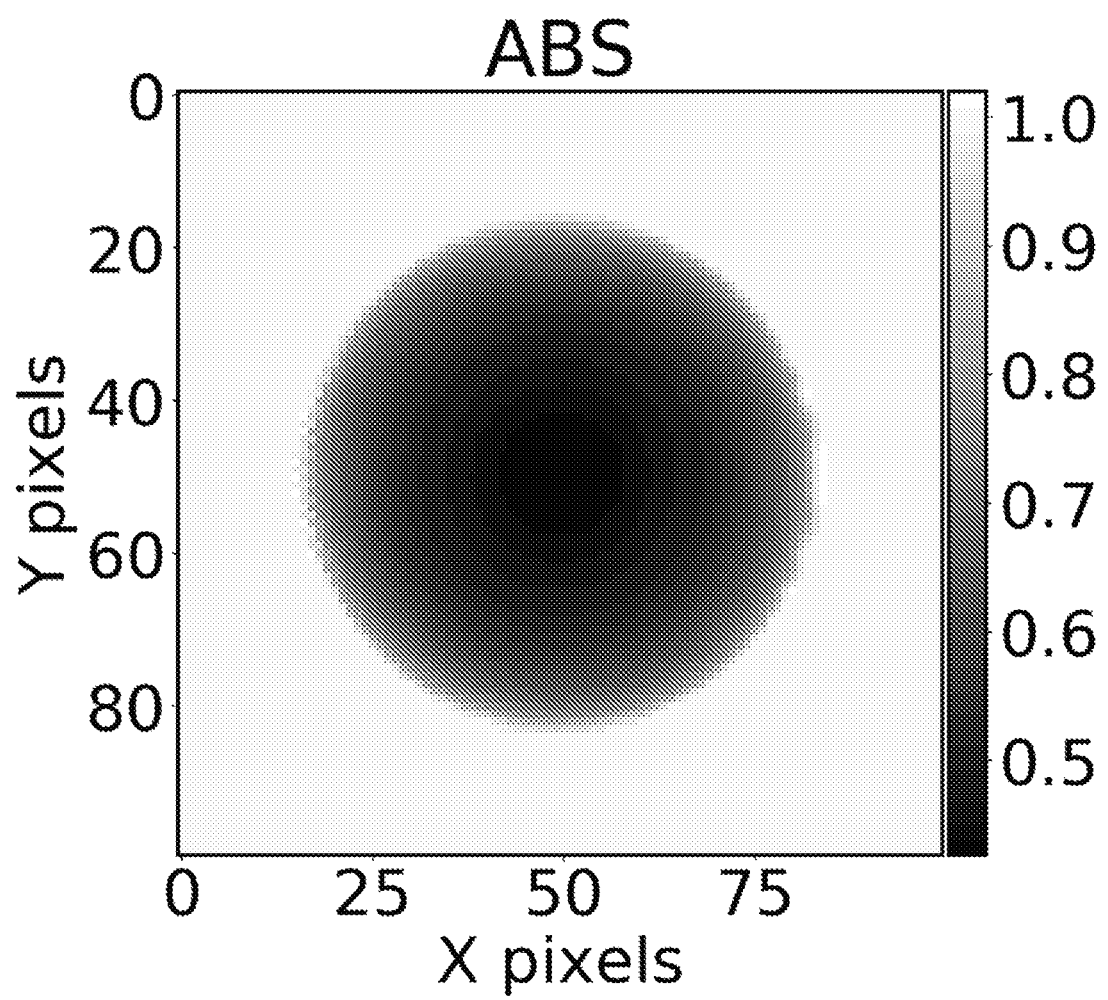
FIG. 8 shows a demodulated attenuation image.
Figure 9:
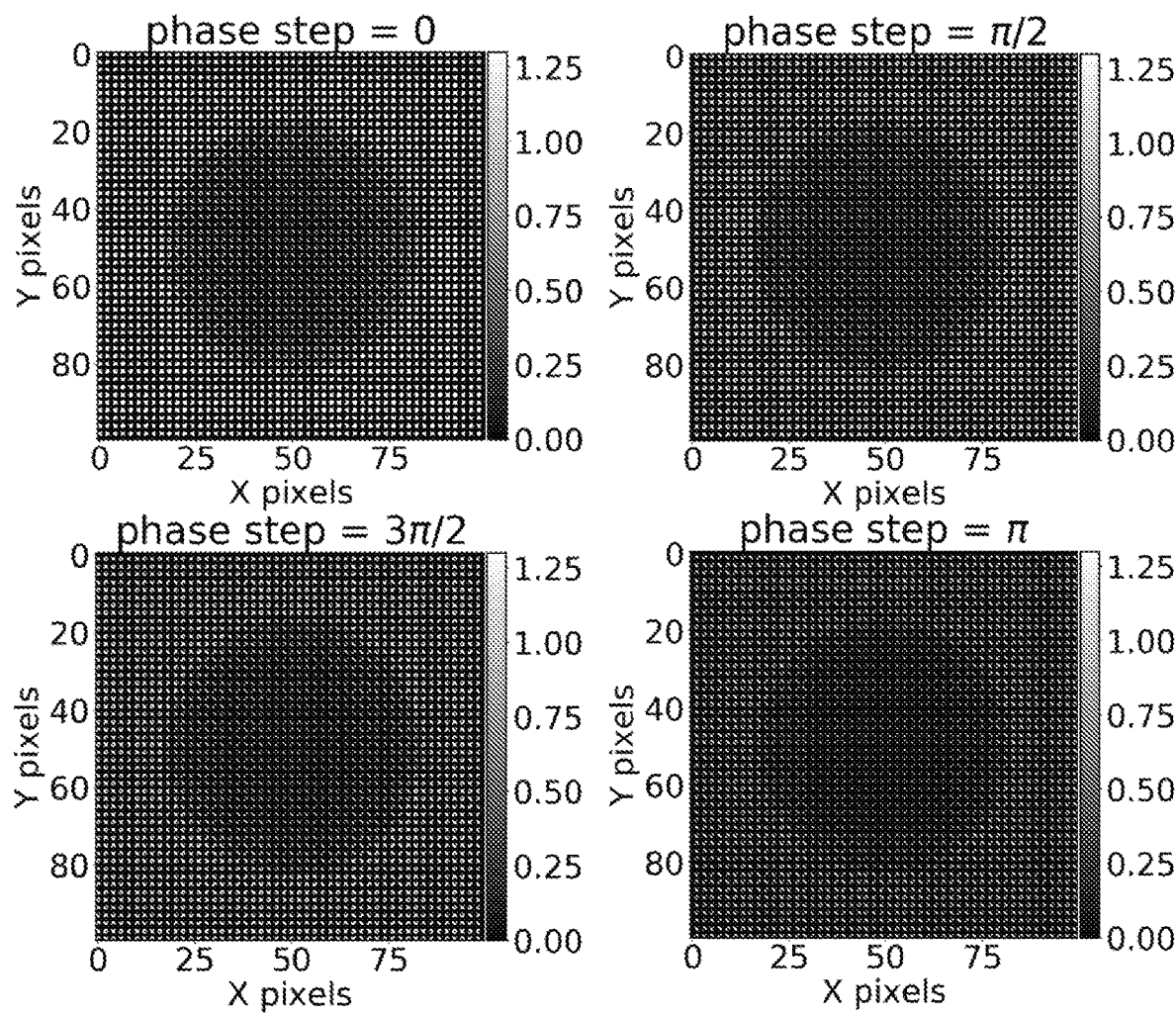
FIG. 9 shows data from different channels.
Figure 10:
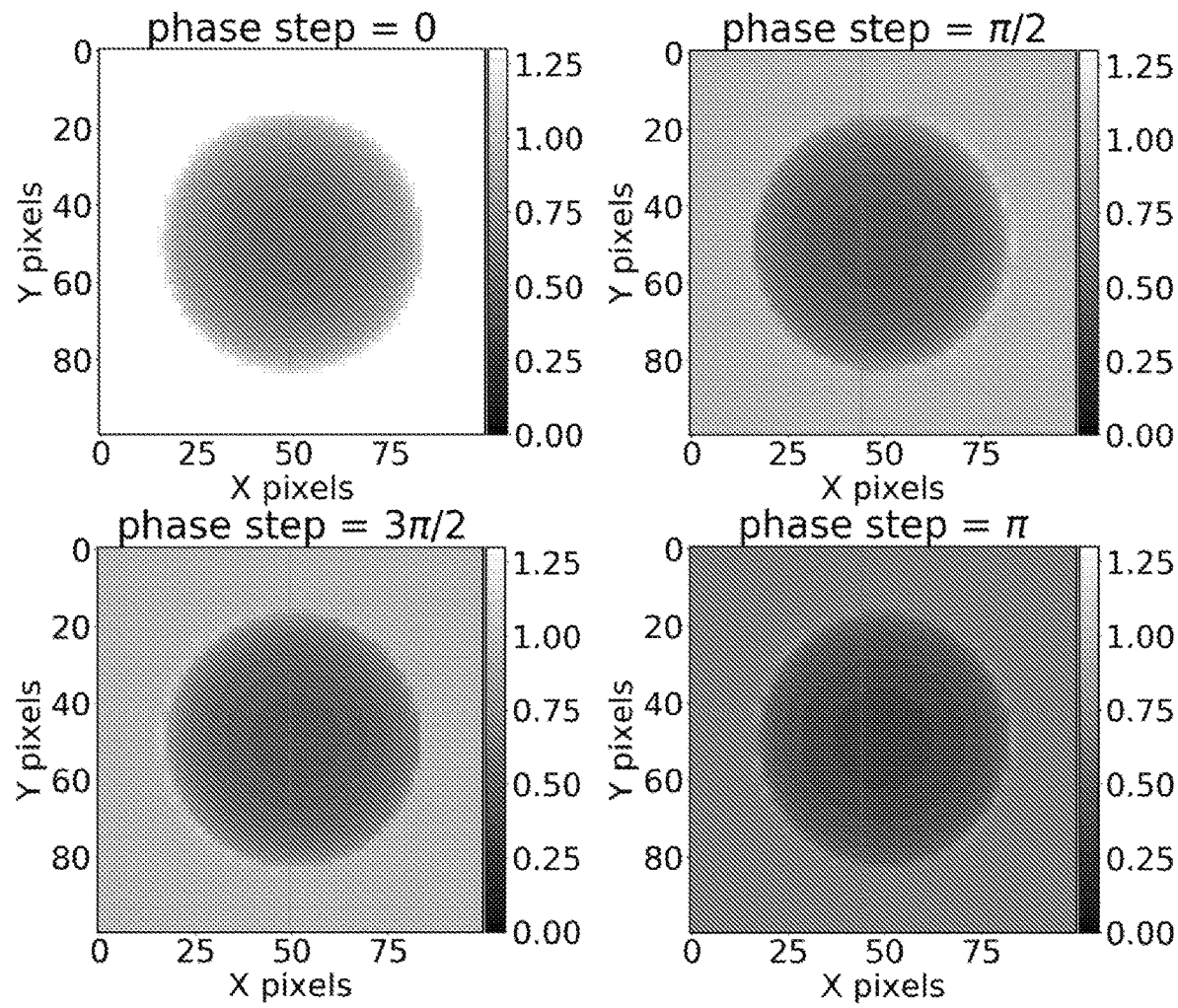
FIG. 10 shows interpolated results from the data of FIG. 9.

Equation 6 is basically a reversed version of Equation 2. Similar to the previous sections, corner pixels belong to one superpixel, edge pixels belong to two superpixels, and interior pixels belong to four superpixels. Thus each processed image pixel is assigned an $I_{0,\ demod}$ value using the mean or median of its $I_{0,\ demod}$ value in its enclosing superpixels. FIG. 8 shows a demodulated attenuation contrast image. This method only applies to the intensity channel The above embodiments were based on the phase-stepping fit of Equation 2 with signals measured at different locations. In a 2×2 SSG scheme, $I^0$, $I^1$, $I^2$ and $I^3$ (the intensity measurements at grating phases $$0, \frac{\pi}{2}, \pi, \text{ and } \frac{3\pi}{2})$$

are each measured in one-fourth of the grating pixels. Another embodiment uses interpolation to assign values of $I^0$, $I^1$, $I^2$ and $I^3$ in all pixels, then uses curve fitting in each pixel separately to obtain three-channel images, exactly as for a conventional temporal phase-stepping scheme. For example, in the SSG grating of FIG. 4, $I^0$ is measured at pixels (1+2i,1+2j) for i,j∈ {0,1,2,3} because the grating phase is zero there (i.e. $2\pi \times G2/p2 = 0$). $I^0$ is approximated in the other pixels by averaging two or four neighboring $I^0$ values, similarly to the interpolation methods described above. The same procedure is used to interpolate $I^1$, $I^2$ and $I^3$. FIG. 9 shows $I^0$, $I^1$, $I^2$ and $I^3$ in their respective pixels, with all other pixels set to zero. FIG. 10 shows the four intensity images after interpolation onto all pixels. Edge values can be assigned by nearest neighbor interpolation or linear extrapolation as necessary.

Figure 11:
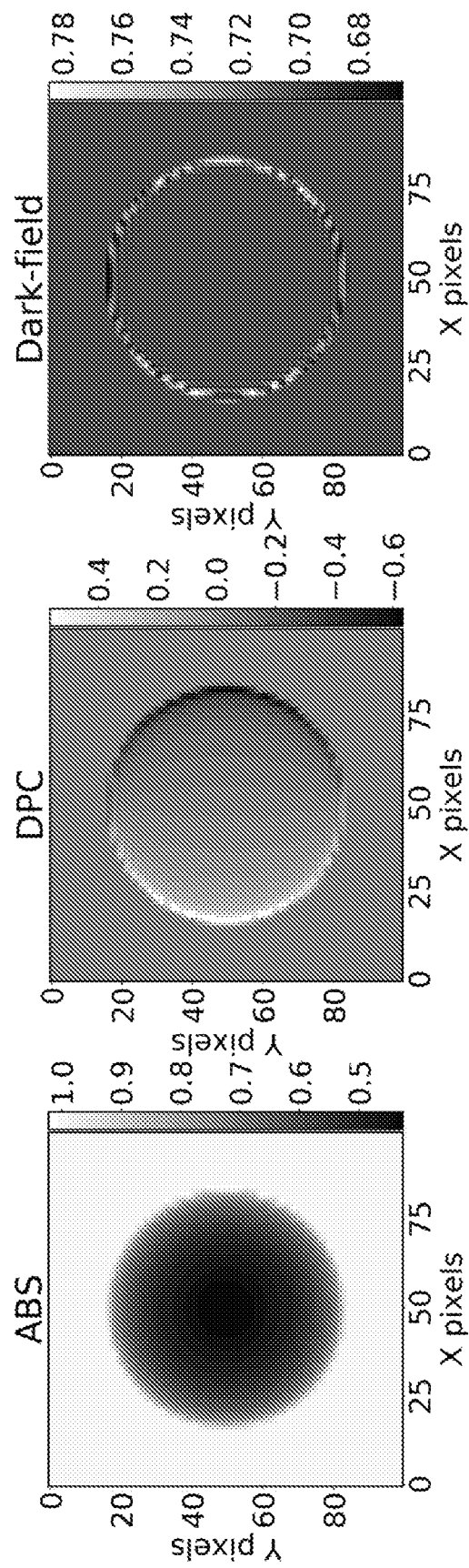
FIG. 11 shows reconstructed images using interpolation.

Once all phase steps are defined in all pixels, fringe parameters are fitted to the data following Equation 2 to yield the three-channel images with the same size and resolution as the SSG image. Reconstructed three-channel images using linear interpolation are shown in FIG. 11. The results are similar to FIGS. 7B-D.

In an embodiment described above, the phase stepping methods were based on an assumption that $I_0$, A and ϕ vary slowly in space. If the fringe parameters vary rapidly, fitting Equation 2 to unrolled SSG data can lead to large errors because the SSG modulation cannot be distinguished from the spatial variation of the fringe parameters. In this embodiment, a method to alleviate the effect of fast changes in intensity is provided. However, the assumption of slow variation in phases is still maintained.

Figure 12:
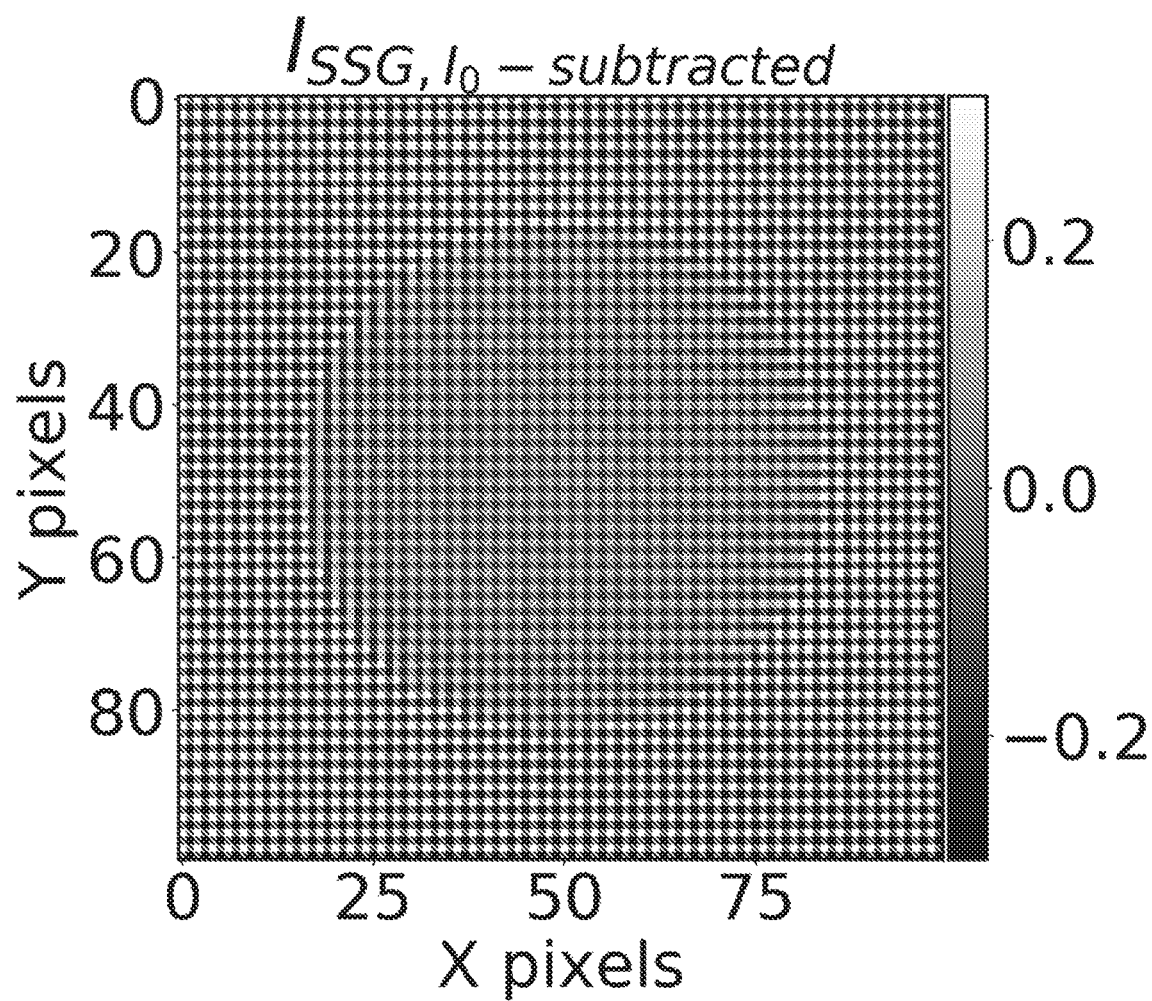
FIG. 12 shows an SSG image with $I_{0,\,demod}$ subtracted.
Figure 13:
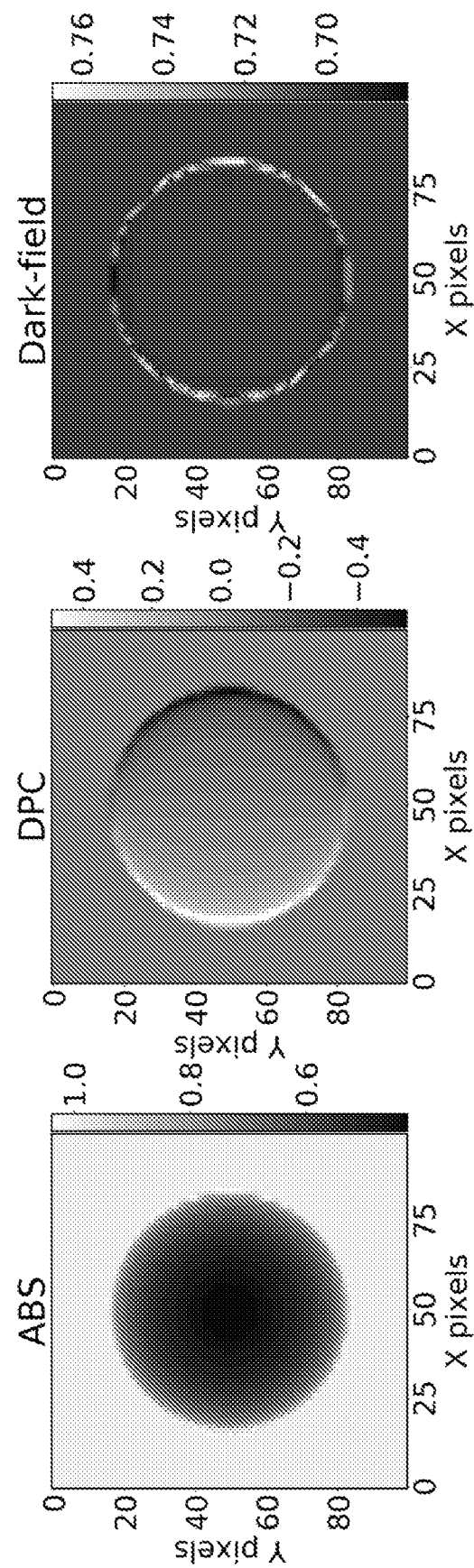
FIG. 13 shows reconstructed three-signature images in an embodiment.

First, the demodulation method described in an embodiment described above (Equation 6) is used to obtain $I_{0,\ demod}$ in each overlapping superpixel at a stride of 1×1, and $I_{0,\ demod}$ is calculated in each grating pixel by mean or median filtering as described earlier. Second, $I_{0,\ demod}$ is subtracted from the SSG image, as shown in FIG. 12:

$$I_{SSG,\ I_0 subtracted} = I_{SSG} - I_{0,\ demod}. \quad [7]$$

The $I_{SSG,\ I_0}$ subtracted is called the "debaselined" signal, i.e. the detected signal minus the DC (intensity) part, measured in each grating pixel. It approximates the oscillating part of Equation 2, with a small residual that can be attributed to the intensity channel $$I^i_{SSG,I_0 subtracted} = A \cos\left(\frac{2\pi x^i_{G2}}{p_2} + \phi\right) + I^i_{resid}. \quad [8]$$

The debaselined signal in each overlapping superpixel is unrolled, curve-fitted, and restored to high resolution by median filtering exactly as described above, yielding debaselined three-channel images $I_{resid}$, A, and ϕ. The intensity image is obtained by adding the set-aside demodulated intensity back to the residual intensity, $I=I_{0,demod}+I_{resid}$. The final three-channel images are (I, ϕ, A).

The above embodiments provided a few simple methods to reconstruct the hidden three signature information using single-shot grating spatially-coded X-ray images. In other embodiments, more complicated algorithms could be applied to further refine the resolution and reduce artifacts beyond the simple reconstruction methods. However, these simple methods are sufficient to get resolution-recovered three signature X-ray images for an X-ray DPC imaging system.

Model-Based Single-Shot Image Analysis

In other embodiments, the SSG image is used to fit a space-dependent parameterized model of the fringe pattern in the X-ray fringe plane. The model defines values of the fringe parameters at arbitrary points (x, y) in the fringe plane, including but not limited to the centers of detector pixels. Rather than assuming that the SSG image pixels can be unrolled into a sinusoidal curve, a model-based method defines a measurement model $$I(x,y;p)=I_0(x,y;p)+A(x,y;p)\cos(\phi(x,y;p)+\psi_G(x,y)) \quad [9]$$

or equivalently $$I(x,y;p)+I_0(x,y;p)+(A\cos(\phi+\psi_G))(x,y;p)-(A\sin(\phi+\psi_G))(x,y;p) \quad [10]$$

which is sampled at pixel locations. In other embodiments, the model may allow non-sinusoidal fringe patterns or other variations. The parameter vector p and the functional form of the measurement model may differ between embodiments. In some embodiments, the parameters are the intensity, amplitude, and phase sampled at points in the image plane, and the measurement model may be an interpolating function between those sample points. In other embodiments, the model may be a superposition of basis functions and the parameters are weights for each basis function. Models may be global, e.g. Fourier basis functions, or local, e.g. finite element method (FEM) basis functions defined in superpixels.

In some embodiments, model parameters are chosen to minimize some figure of merit depending on parameters and the measured SSG image. Such methods resemble curve-fitting. Then the model can be evaluated at arbitrary points (x, y) to recover the three-channel image at arbitrary resolution. Regularization or other methods may be employed to compel the model to favor more-realistic fringe patterns.

The performance of a model (accuracy, noise, bias) is affected by the pattern of the SSG. The SSG can be designed in tandem with a model-based analysis method to optimize the end-to-end performance of the X-ray DPC imaging system.

Design of Single-Shot Gratings

In the above embodiments, the third grating 116, analyzer amplitude grating (G2), has the grating pixel phases shown in FIG. 4. In these embodiments, 2×2 SSG patterns of different phases are defined. The phase differences are created as shown in FIG. 3A, where the grating lines provide phase variations made into the grating 116. In some embodiments, two grating pixels are deemed adjacent if they are "4-adjacent", i.e. if they share an edge. Two grating pixels are not deemed adjacent if they only share a corner. In other embodiments, two grating pixels are deemed adjacent if they are "8-adjacent", i.e. if they share an edge or share a corner. In embodiments where alternating rows or columns of grating pixels are staggered, an edge of a grating pixel may abut more than one neighboring pixel, and two pixels could be deemed adjacent if they share an entire edge, or alternatively if they share part of an edge. In this embodiment, pixels are adjacent if they are 4-adjacent. As shown, each grating pixel has a different pattern in that each grating pixel has a different pattern with respect to all adjacent grating pixels, so that no pair of adjacent grating pixels have the same pattern. Examples of "different patterns" are given above. For example, at grating pixel (2,2) in FIG. 4, the phase shift of the grating pixel is π. The grating for the phase shift of π is shown as the fourth grating pixel 316 in FIG. 3A. The adjacent grating pixels to grating pixel (2,2) are grating pixels ((2,1), (3,2), and (2,3). None of the grating pixels that are adjacent to grating pixel (2,2) have a phase shift of π. Therefore, the grating pixel (2,2) 316 has a shifted pattern with respect to all adjacent grating pixels.

In various embodiments, the third grating 116 is part of an interferometric imaging system that is located at or near an X-ray fringe plane. The third grating 116 is placed sufficiently close to the fringe plane to allow a difference between the pitch of the fringe pattern and the pitch $p_2$ of the third grating 116 to be within 5% of each other. With the difference between the pitch of the fringe pattern and pitch of the third grating 116, the difference between the pitch of the fringe pattern and fringe of the third grating 116 is ±5%, providing a tolerance of 5%. At such a location of the third grating 116, the fringe pattern has a sufficient focusing of the fringe pattern on the third grating 116 to allow for the measurement of the fringe pattern. The pitch of the fringe pattern is related to the distance of the fringe plane from the X-ray source and the energy of the X-ray source, as described above. In various embodiments, the X-ray energy of X-rays from the X-ray source range from 1 keV to 1 MeV. In such embodiments, the third grating 116 has a pitch in the range of 50 nm to 500 microns.

In various embodiments, the unit cells of the third grating 116 may be at least one of 2×2, 3×2, 2×3, 3×3, or 4×4. Other third gratings 116 in other embodiments may have other sizes of unit cells.

In this embodiment, the X-ray detector 120 has a detector pixel size in the range from 500 nm to 50 mm In various embodiments, a grating pixel of the third grating 116 corresponds with a single adjacent pixel of the X-ray detector. In such an embodiment, X-rays passing through a grating pixel are directed to a single pixel of the X-ray detector. In other embodiments, a grating pixel corresponds to 1×2 adjacent detector pixels or 2×1 adjacent detector pixels or 2×2 adjacent detector pixels, or 3×3 adjacent detector pixels. Other embodiments may have the grating pixel correspond with other pluralities of adjacent detector pixels.

In the embodiment shown in FIG. 3B, the third grating 116 has a one-dimensional grating pattern, in that the grating has a pitch $p_2$ in one direction and does not vary in the other direction; for example, a grating of parallel slits. In other embodiments, the third grating 116 has a two-dimensional grating pattern that is periodic in two dimensions; for example, a grating of apertures repeating in both horizontal and vertical directions. In other embodiments, the changed pattern between grating pixels is achieved by changing the pitch $p_2$ between grating pixels.

In other embodiments, the pattern of grating pixel phases is designed to maximize phase sensitivity, minimize the effect of image noise, or minimize three-channel image artifacts arising from the spatial variation of the fringe parameters.

In other embodiments, the pattern of grating pixel phases is not periodic, but still, no pair of adjacent grating pixels has the same phase shift. The grating pixel phases may be random or quasi-periodic.

In other embodiments, irrespective of the grating pixel phase, the grating within each grating pixel is not uniform, but "chirped" so its pitch varies from $p_2-\Delta p$ to $p_2+\Delta p$ from one side of the grating pixel to the other. By chirping the grating within each grating pixel, the transmission through the analyzer grating can be made less sensitive to changes in the period of the fringe pattern that may arise due to misaligned optical components or other causes.

In most of the embodiments described in the previous paragraphs, the algorithms assume slowly varying intensity and phase of the detected signals. This assumption is usually valid within the bulk of imaged objects. However, at objects' edges, the intensity, phase, and amplitude may have step variations or even spikes. The drastic changes of these signals are usually the main sources of SSG reconstruction error. Furthermore, these changes frequently occur over the distance of a single pixel or less and are difficult to model. Therefore, in some embodiments, artificial intelligence (AI) algorithms are applied to analyze the SSG image and recover improved three-channel images. More specifically, machine learning (or deep learning) is used to train neural network models of superpixels, larger image sub-regions, or even entire SSG images; and these models convert SSG data to three-channel contrast images.

Figure 14:
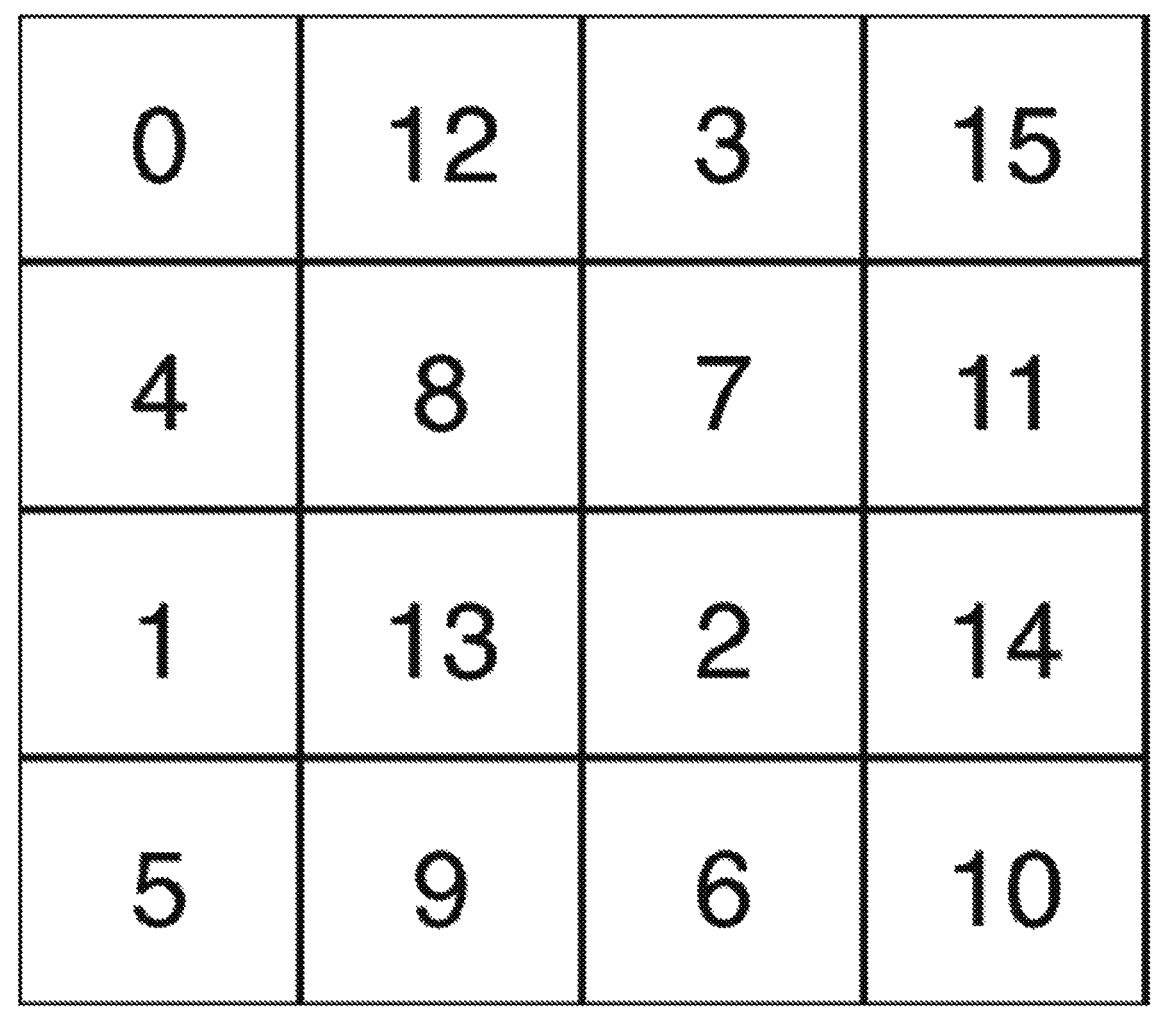

FIG. 14 is a table showing phase shifts for grating pixels for a 4×4 unit cell used in another embodiment. The numbers in the table are a phase index n=0, 1, . . . , 15, where in this embodiment the phase shift is calculated by $\phi=2n\pi/16$. Because of the larger unit cell, this embodiment may provide a smoother and more accurate phase map. The 4×4 unit cell is made up of four 2×2 sub-arrays.

Figure 15:
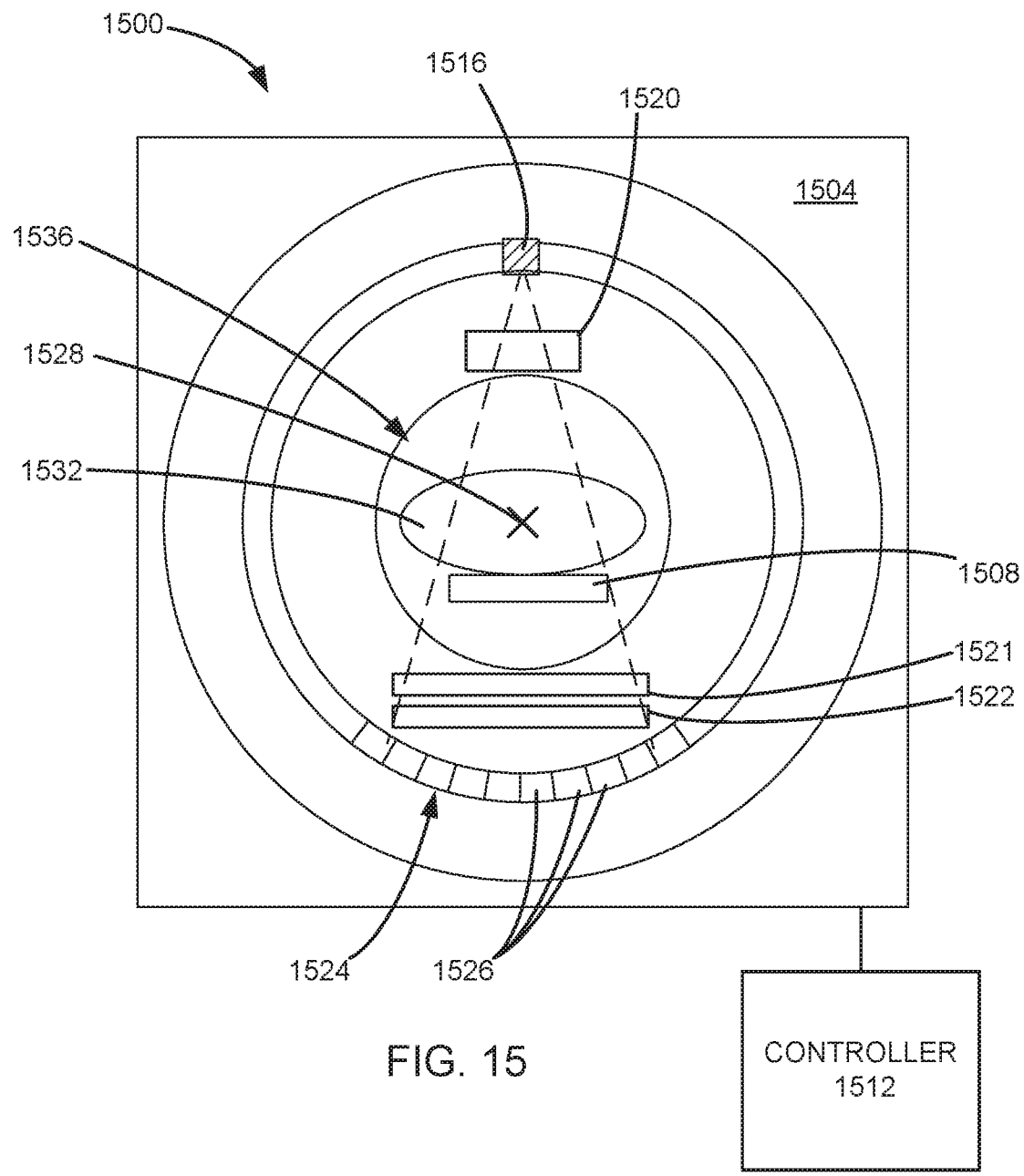
FIG. 15 is a schematic view of a computed tomography system of another embodiment.

FIG. 15 is a schematic view of a system of an embodiment. A differential phase contrast imaging computed tomography (CT) system 1500 comprises a gantry 1504, a support 1508, a first amplitude grating 1520, a phase grating 1521, a second amplitude grating 1522, and a controller 1512. The gantry 1504 supports an X-ray source 1516, the first amplitude grating 1520, the phase grating 1521, the second amplitude grating 1522, and an X-ray detector 1524. The X-ray detector 1524 has detector elements 1526, where the detector elements 1526 have a width. The gantry 1504 rotates the X-ray source 1516, first amplitude grating 1520, the phase grating 1521, the second amplitude grating 1522, and X-ray detector 1524 around an axis of rotation 1528 that extends into the page. The support 1508 supports an object 1532 to be scanned. The support 1508 or gantry 1504 translates the object 1532 with respect to the X-ray source 1516, the first amplitude grating 1520, the phase grating 1521, the second amplitude grating 1522, and X-ray detector 1524 along the axis of rotation 1528 through an aperture 1536 in the gantry 1504. In this embodiment, the X-ray source 1516 provides a collimated beam that has a cross-section with a length and thickness. The axis of rotation 1528 is substantially perpendicular to the length of the cross-section of the collimated beam. In other embodiments, other grating configurations may be provided.

Figure 16:
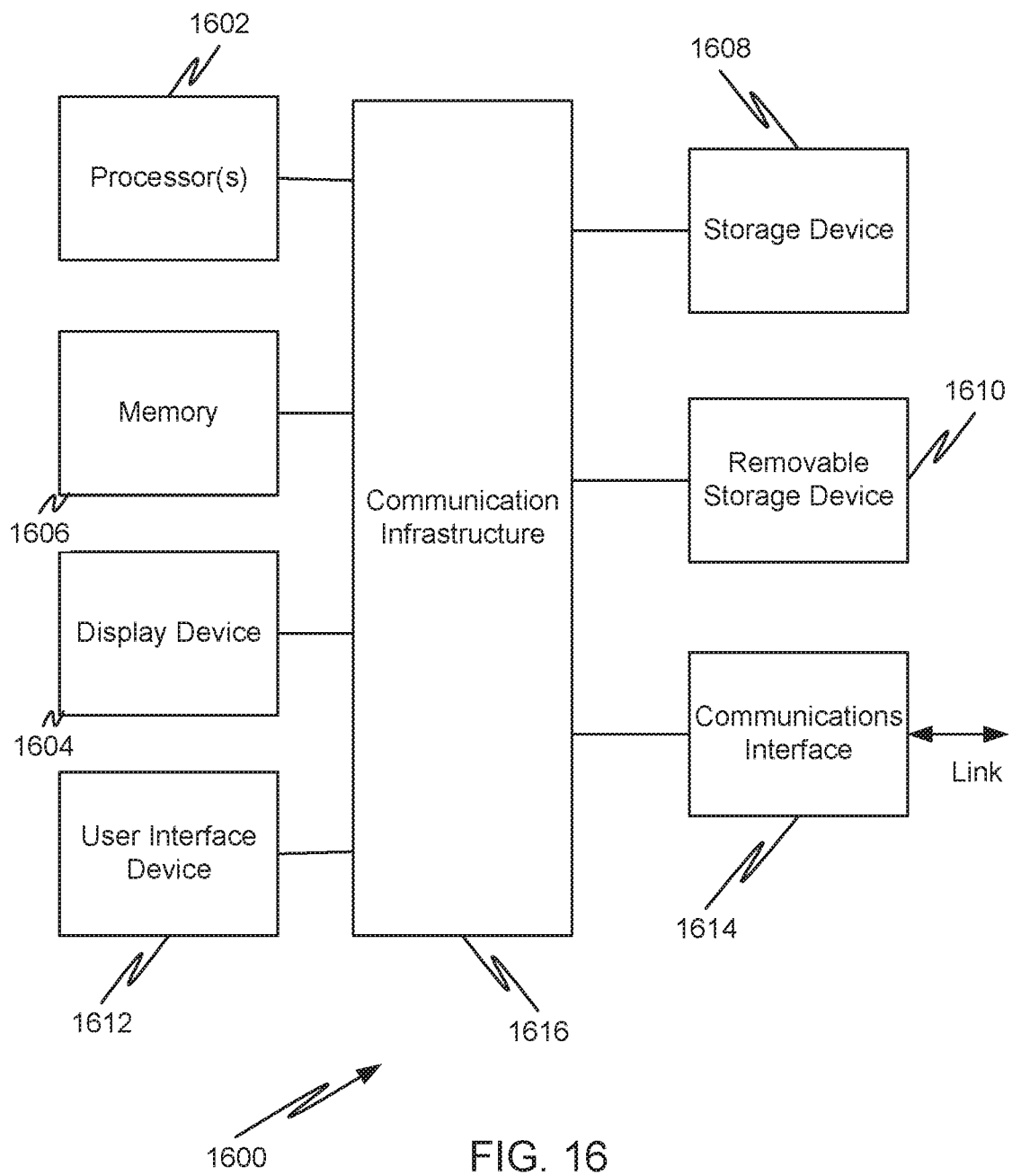
FIG. 16 illustrates a computer system that may be used in an embodiment.

FIG. 16 is a high-level block diagram showing a computer system 1600, which may be used to provide the controller 1512. The computer system may have many physical forms ranging from an integrated circuit, a printed circuit board, and a small handheld device up to a computer. The computer system 1600 includes one or more processors 1602, and further can include an electronic display device 1604, a main memory 1606 (e.g., random access memory (RAM)), data storage device 1608 (e.g., hard disk drive), removable storage device 1610 (e.g., optical disk drive), user interface devices 1612 (e.g., keyboards, touch screens, keypads, mice or other pointing devices, etc.), and a communication interface 1614 (e.g., wireless network interface). The communication interface 1614 allows software and data to be transferred between the computer system 1600 and external devices via a link. The system may also include a communications infrastructure 1616 (e.g., a communications bus, cross-over bar, or network) to which the aforementioned devices/modules are connected.

Information transferred via communications interface 1614 may be in the form of signals such as electronic, electromagnetic, optical, or other signals capable of being received by communications interface 1614, via a communication link that carries signals and may be implemented using wire, cable, fiber optics, a phone line, a cellular phone link, a radio frequency link, and/or other communication channels. With such a communications interface, it is contemplated that the one or more processors 1602 might receive information from a network, or might output information to the network in the course of performing the above-described method steps. Furthermore, method embodiments of the present invention may execute solely upon the processors or may execute over a network such as the Internet in conjunction with remote processors that share a portion of the processing.

The term "non-transient computer readable media" is used generally to refer to media such as main memory, secondary memory, removable storage, and storage devices, such as hard disks, flash memory, disk drive memory, CD-ROM, and other forms of persistent memory and shall not be construed to cover transitory subject matter, such as carrier waves or signals. Examples of computer code include machine code, such as produced by a compiler, and files containing higher level code that are executed by a computer using an interpreter. Computer readable media may also be computer code transmitted by a computer data signal embodied in a carrier wave and representing a sequence of instructions that are executable by a processor.

In this embodiment, the second amplitude grating 1522 is a 4×4 SSG. In some embodiments, a 3D reconstruction using CT may be provided without performing a 2D reconstruction. Therefore, a phase shift determination for a 2D reconstruction is not needed. Instead, a forward model may be constructed, parameterized by material properties in the volume such as the attenuation coefficient $\mu(x, y, z)$, refractive index decrement $\delta(x, y, z)$, and linear scattering coefficient $\varepsilon(x, y, z)$; and producing SSG images at all ray angles used in tomography, $l(i, j, \theta)$, for row i, column j, and ray angle $\theta$. The SSG images taken at each angle are collectively the SSG sinograms. The model may represent monochromatic tomography, or it may represent polychromatic tomography where $\mu(x, y, z; E)$, $\delta(x, y, z; E)$, and $\varepsilon(x, y, z; E)$ are functions of photon energy E as well as position. The material properties in the volume may be represented by samples in a grid, called voxelized material properties. The forward model will map the material properties in the volume to expected SSG sinograms which more or less closely match the experimentally measured SSG sinograms. The difference between the modeled SSG sinograms and the measured SSG sinograms is the SSG residual. Numerical methods such as nonlinear least squares minimization can be applied to find voxelized material properties that minimize the norm of the SSG residual under the action of the forward model. Other discretization schemes may be used for the material properties. Other numerical methods may be used to minimize the SSG residual. Some numerical methods may use criteria other than the minimized residual to define the optimal material properties. For purposes of 3D reconstruction using CT, some SSG designs may be more favorable than others. For instance, if the CT axis of rotation is parallel to the column direction of the SSG images, it may be desirable to ensure that the grating pixel phases in each row of the SSG unit cell evenly sample the interval $[0,2\pi]$. The SSG unit cell of FIG. 3B does not meet this criterion, because its top-row phases are grouped closely, and its bottom row phases are grouped closely. Instead, a unit cell with grating pixel phases 0 and $\pi$ on the top row and $\frac{\pi}{2}$ and $\frac{3\pi}{2}$ on the bottom row might be more favorable. An SSG pattern might also be designed to minimize the sensitivity of CT reconstruction to detector noise, maximize phase sensitivity, or maximize the ability to resolve sharp edges. Such design criteria would be directly defined in terms of CT reconstruction, without the intermediate step of calculating three-channel images. In some embodiments, each slice of the object to image might be imaged by only one row or only some rows of the SSG. For example, with a 2×2 unit cell, even-numbered slices of the object might be imaged only by even-numbered rows of the SSG, and odd-numbered slices of the object might be imaged only by odd-numbered rows of the SSG. In other embodiments, each slice of the object to image might be imaged by all rows of the SSG. The SSG will be designed with knowledge of which SSG pixels will image which parts of the object.

In various embodiments, the computer readable media may comprise computer readable code for receiving X-ray detection data for a single shot from the X-ray detector and computer readable code for using the X-ray detection data for a single shot to create an image of the object. In using the X-ray detection data to create an image, measured variations in the X-ray detection data corresponding to adjacent grating pixels are used to create the image of the object.

Figure 17:
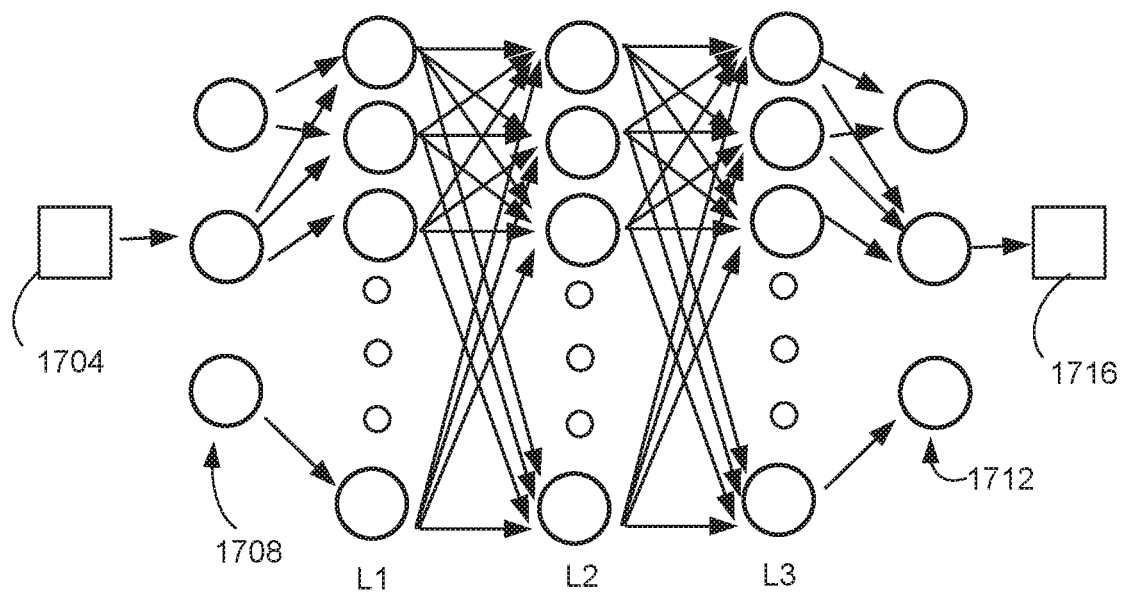
FIG. 17 shows a dense neural network.

In other embodiments, artificial intelligence may be used to process collected data. FIG. 17 shows an exemplary dense neural network (DNN) that may be used in an embodiment. A DNN comprises a plurality of layers, including an input layer 1708, at least one hidden layer L1 (L2 and L3 and more if using multiple hidden layers), and an output layer 1712, each comprising a plurality of nodes. The nodes in each layer are connected to the nodes in either the upstream, downstream, or both upstream and downstream layers by an affine combination with an optional follow-up nonlinear operation:

$$a^{[l]} = f^{[l]}(W^{[l]} a^{[l-1]} + b^{[l]}) \quad [11]$$

where $W^{[l]}$ is the weight vector of layer l, $a^{[l-1]}$ is the input node vector fed from either the input layer or the previous l-1 layer, $b^{[l]}$ is a bias added as a regularization factor, and $a^{[l]}$ is the output signal of the current l layer. The activation function $f^{[l]}$ is used to introduce nonlinearity, so that the neural network is able to fit a more complicated model. Common activation functions include the sigmoid function, rectified linear unit (ReLU), and leaky ReLU; $f^{[l]}$ can also be the identity function, in which case the node's behavior is purely affine. In some embodiments, an input image section 1704 (further described in FIG. 19A-D) is used as the input to feed the raw or processed signals to the DNN, and the output of the DNN is the input to the output image section 1716 (further described in FIG. 20A-B). In some embodiments the number of layers may be quite large, dozens or hundreds or more, to support complex models.

Figure 18:
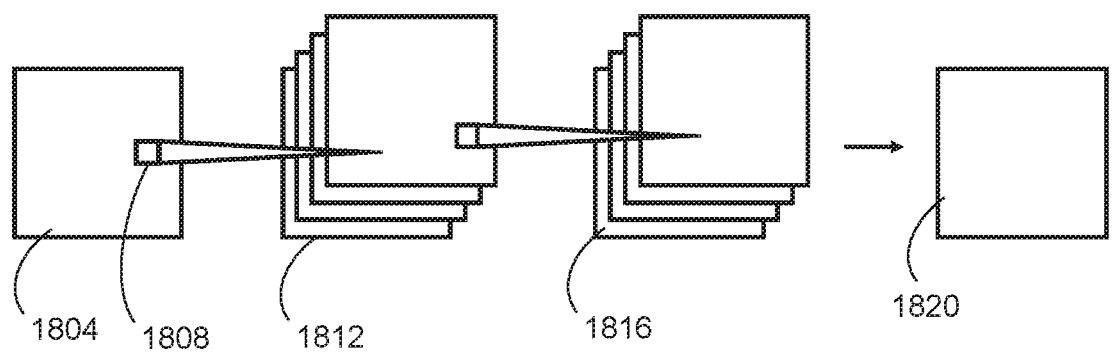
FIG. 18 shows a convolutional neural network.

FIG. 18 shows an exemplary convolutional neural network (CNN). A CNN comprises an operation of a plurality of convolution kernels 1808 of sizes m×n pixels with c filters. A single layer of a CNN carries out the nonlinear stencil operation $$a^{[l]}_{c_{out,i}} = f^{[l]} \left( \sum_{k=1}^{c_{in}} \left[ W^{[l]}_{c_{out,i}, c_{in,k}} * a^{[l-1]}_{c_{in,k}} + b^{[l]}_{c_{out,i}} \right] \right) \quad [12]$$

where $W^{[l]}_{c_{out,i}, c_{in,k}}$ is the convolution kernel of layer l, $c_{in,k}$ is the k-th CNN data channel from the l−1 layer, and $c_{out,i}$ is the i-th CNN data channel to be outputted in the layer l. $a^{[l-1]}_{c_{in,k}}$ is the data input from the k-th CNN data channel of the layer l−1, $a^{[l]}_{c_{out,i}}$ the data output from the i-th CNN filter channel of the layer l, and $b^{[l]}_{c_{out,i}}$ is the bias term for the i-th CNN filter channel A nonlinear activation function $f^{[l]}$ is commonly used, similarly to DNNs. In the convolutional operation described in Equation 12, the convolution kernel $W^{[l]}_{c_{out,i}, c_{in,k}}$ each layer is a stencil operation, moving the convolution kernel 1808 in both directions of the two-dimensional filtered image in each channel with a stride of one or more pixels. In an embodiment, an input image section 1804 (further described in FIG. 19A-D) is an input layer 1804 of a CNN. The input layer is fed to the first CNN layer 1812, and the output of the first CNN layer 1812 is fed to the second CNN layer 1816. The output of the CNN layer 1816 is the output image section 1820. Possible output data flows in embodiments are shown in FIG. 20A-B. In other embodiments, more convolutional layers may be composed to build a deeper CNN, implementing a more complicated model.

Figure 19A:
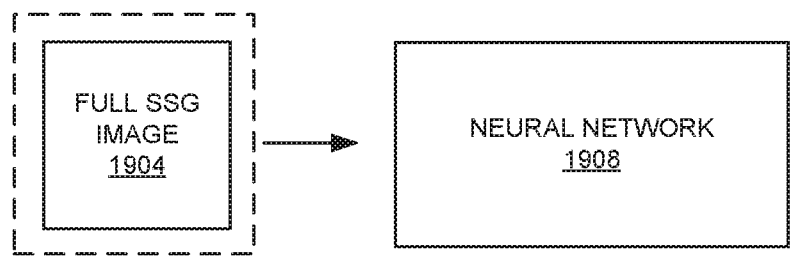
FIG. 19A shows an image input section in an embodiment.
Figure 19B:
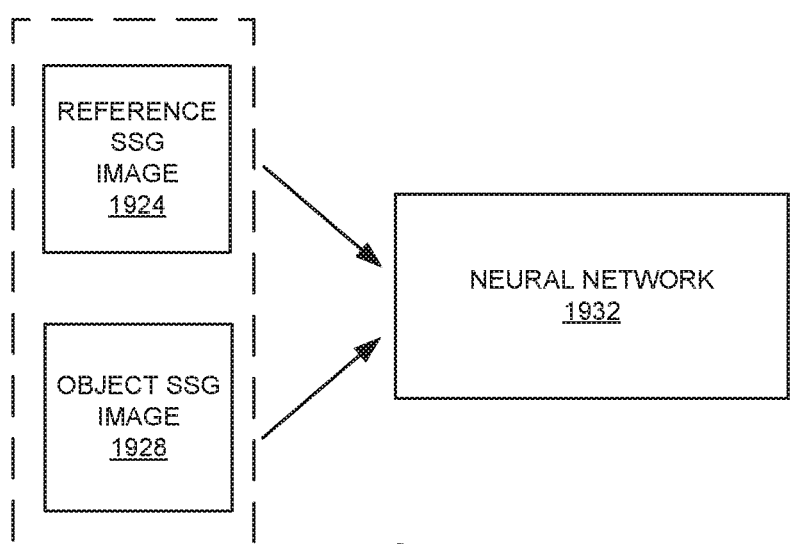
FIG. 19B shows an image input section in another embodiment.

FIGS. 19A-D show examples of how SSG images can be input into neural network models. In some embodiments, the input data to the neural network 1908 is one full SSG image detected by the X-ray detector 120, as shown in FIG. 19A. In other embodiments, especially in the neural network training process (FIG. 22A), the input data to the neural network 1908 can be a "batch" of full SSG images 1904. The number of input images in the batch is usually called the batch size. In other embodiments, the input data to the neural network 1932 can be a pair comprising a reference SSG image 1924 and an object SSG image 1928, as shown in FIG. 19B. In other embodiments, the input data to the neural network can be a batch of pairs of reference SSG images and object SSG images.

Figure 19C:
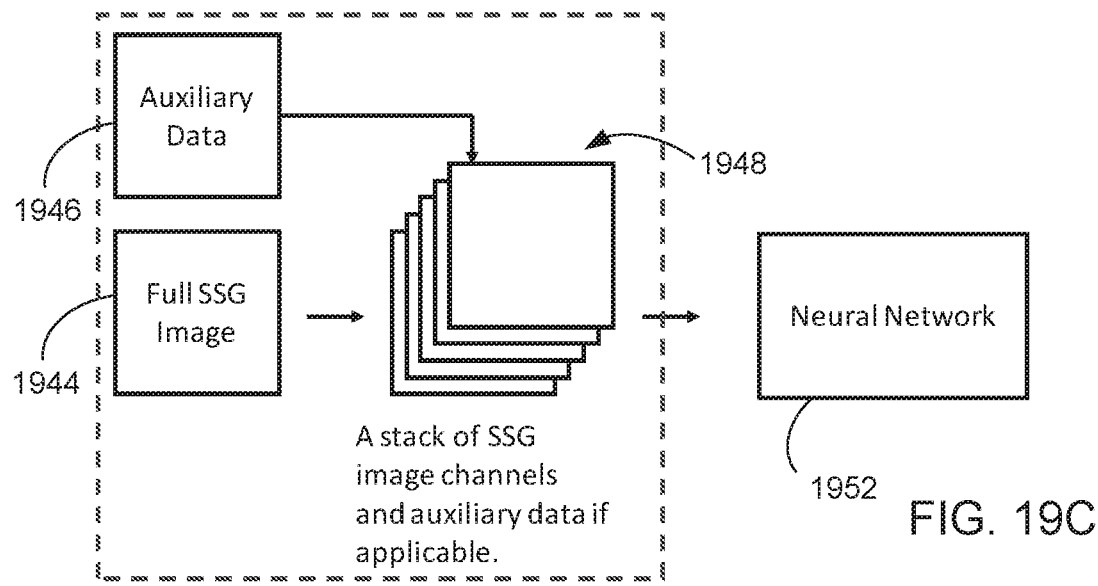
FIG. 19C shows an image input section in another embodiment.
Figure 19D:
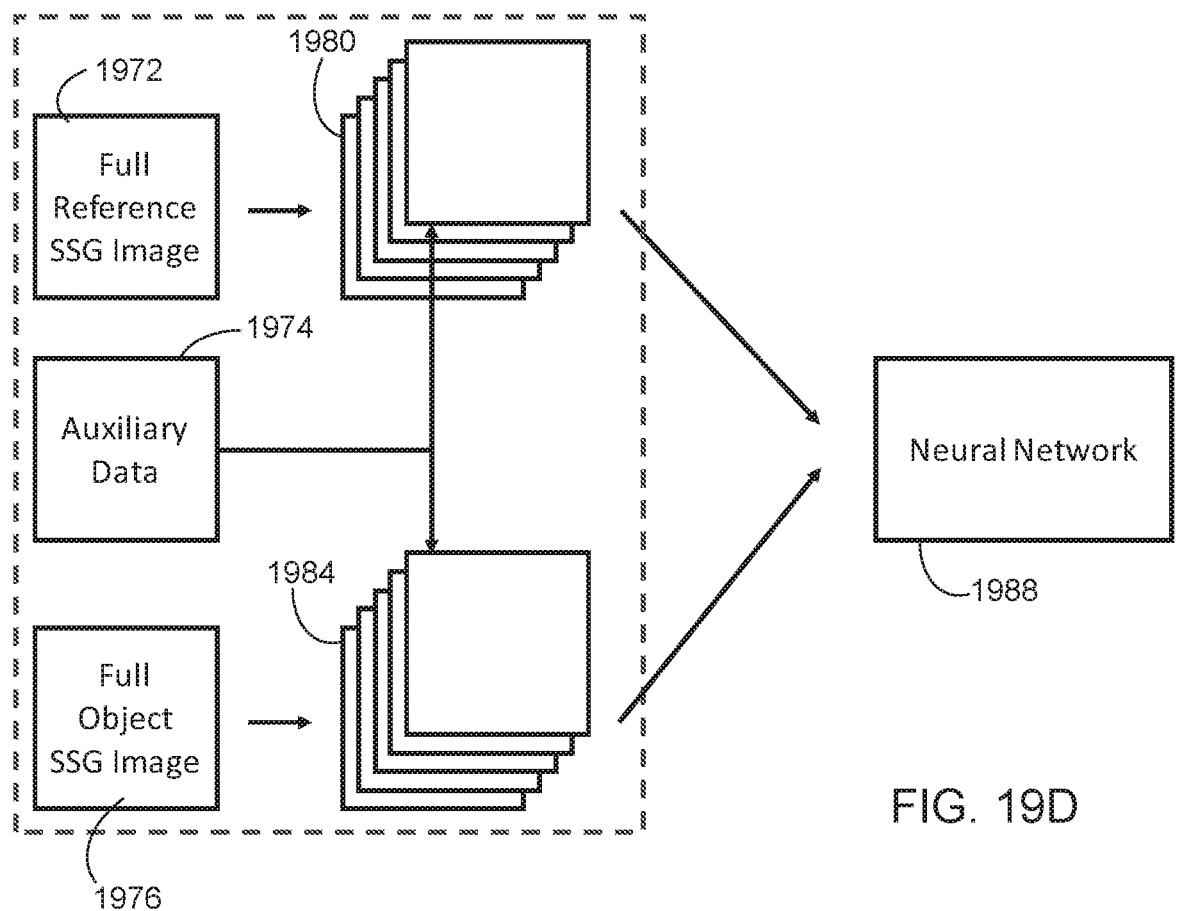
FIG. 19D shows an image input section in another embodiment.
Figure 20A:
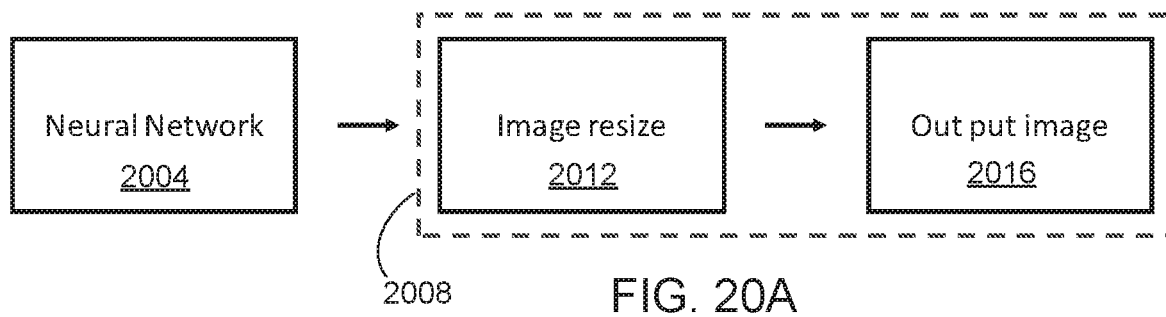
FIG. 20A shows an image output section in an embodiment.
Figure 20B:
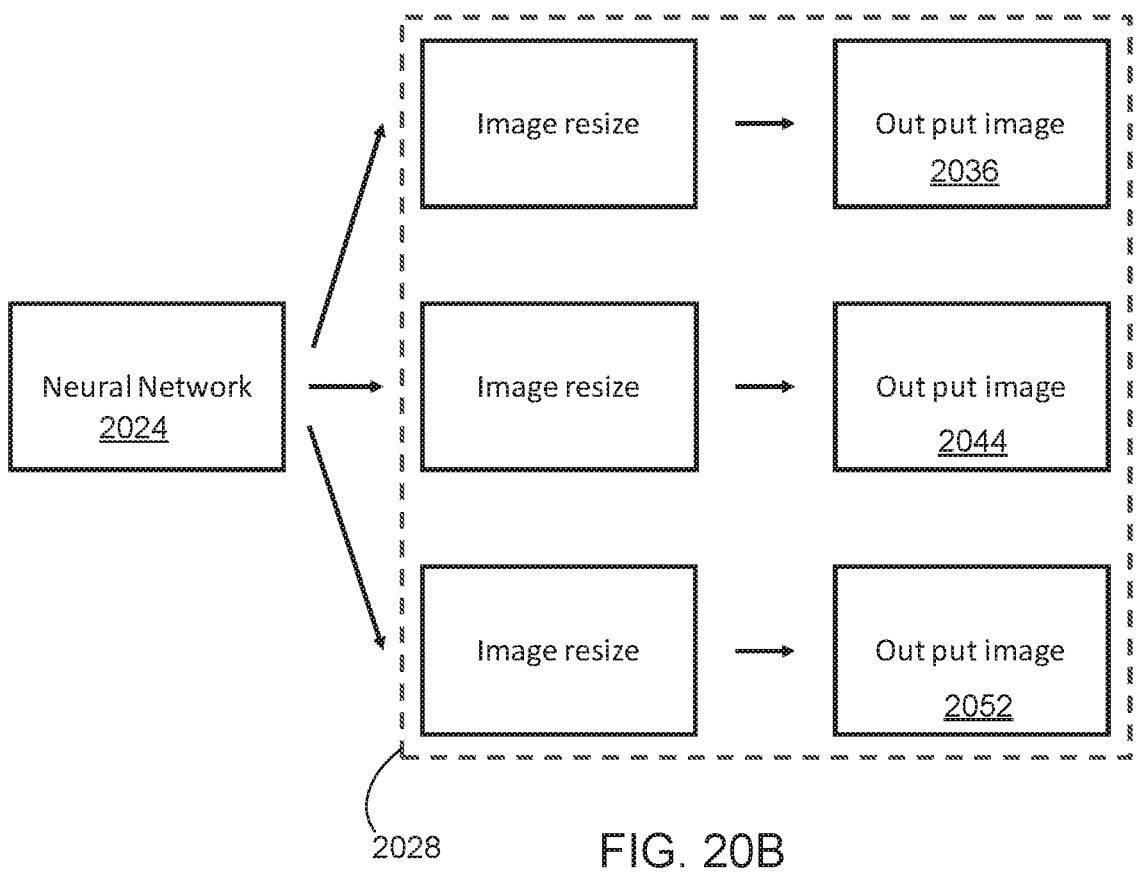
FIG. 20B shows an image output section in another embodiment.

Instead of directly feeding raw SSG images into the neural networks, the image input to the neural networks can be preprocessed with an image processing technique such as resizing the raw images, denoising the raw images, separating the full raw images into sub-sections, etc., or a combination of a plurality of these image processing methods. FIG. 19C exemplifies an image preprocessing method used in an embodiment. In this embodiment, a full SSG image 1944 is separated into a plurality of channels, for example, the four different grating pixels, 304, 308, 312, and 316, used in an SSG unit cell shown in FIG. 3A. The four different input image channels would resemble the four figures shown in FIG. 9 with or without the blank data pixels. In an embodiment, an SSG image of size 2M×2N pixels is duplicated to four image channels of size 2M×2N pixels. Each image channel preserves pixels corresponding to one pixel of the SSG unit cell, and the remaining pixels corresponding to the other three pixels of the SSG unit cell are set to zero, identical to the four subplots of FIG. 9. In another embodiment, an SSG image of size 2M×2N pixels is separated into four image channels of size M×N; pixels of each image channel are copied from pixels of the SSG image corresponding to one pixel of the SSG unit cell; this is identical to removing the zero-valued pixels from the four subplots of FIG. 9. These image channels are stacked together to form the three-dimensional data 1948 in FIG. 19C. In some embodiments, additional non-image data 1946 may be known about the system, such as the map of bad pixels, the expected noise level in each pixel or globally, or some other cause of the systematic error. This non-image data 1946 is scaled to the size of the SSG channels and concatenated with them to form augmented pixel data 1948. This may be used to train the network 1952 to denoise images or for other purposes. In other embodiments, the input image for the neural network 1988 comprises a pair of a full reference SSG image 1972 and a full object SSG image 1976 that are both separated into image channels corresponding to pixels of the SSG unit cell, as shown in FIG. 19D. In some embodiments, two-dimensional non-image data 1974 are concatenated with the SSG channels of the reference and object images 1980 and 1984. In other embodiments, the input image section comprises a batch of processed images described in FIG. 19C and FIG. 19D.

FIGS. 20A-B show examples of the output image section 2008 that can be outputted from the neural network models. In some embodiments, the output image 2016 is one of the three channel images $I_0$, $\phi$, A, or a combination of these images described in Equation 2, as shown in FIG. 20A. In some embodiments where the input to the neural network 2004 includes both reference SSG images and object SSG images, the output image 2016 is one of the three-channel contrast images, ABS, DPC, and DF images. In other embodiments, the output image 2016 is resized in an additional operation 2012. In other embodiments, if the input of the neural network 2004 comprises a batch of input images, one output image is produced for each input image. In other embodiments, the output image section 2028 of the neural network 2024 comprises the three-channel images $I_0$, $\phi$, A, or a combination of these images (2036, 2044, and 2052) described in Equation 2 as shown in FIG. 20B. In other embodiments where the input to the neural network 2024 includes both reference SSG images and object SSG images, the output image 2036 from the neural network 2024 comprises the three-channel contrast images, ABS, DPC, and DF (2036, 2044, and 2052). In other embodiments where the input to the neural network 2024 comprises a batch of input images, the number of output images 2036 would be three times the batch size.

FIGS. 21A-B show a variety of ways to connect a neural network to another neural network or other neural networks. In some embodiments, as shown in FIG. 21A, a neural network 2104 can be connected to another neural network 2018 or to a plurality of neural networks (2018 and 2112) in series such that the output of each neural network except the last is the input of a subsequent neural network. In some embodiments, the output of a neural network 2120 can be split into a plurality of input data fed into a plurality of neural networks (2124, 2128, and 2132), or the output of a neural network can be used as the input fed into a plurality of branches of neural networks (2124, 2128, and 2132), as shown in FIG. 21B. In some embodiments, the outputs of a plurality of neural networks (2140, 2144, and 2148) can be merged together and used as the input to another neural network 2152 as shown in FIG. 21C.

One of the most successful machine learning techniques is supervised learning. In supervised learning, one needs to provide labeled data to be compared with the output data by feeding a neural network model with the paired input data. In some embodiments, when using the neural network 2212 as for supervised learning, as shown in FIG. 22A, a plurality of pairs of an input SSG image 2208 and training $I_0$, $\phi$, or A images 2224, described in Equation 2, are provided. A loss function 2228 can be defined which quantifies the difference of the training $I_0$, $\phi$, or A images 2224 and the output $I_0$, $\phi$, or A images 2220. Using an optimization algorithm to minimize the loss function 2228, the weights, convolution kernels and the bias described in Equation 11 and 12 can be optimized. Through an iterative training process, the output $I_0$, $\phi$, or A images 2220 by feeding the paired input SSG image 2208 through the neural network model 2212 become closer to the training $I_0$, $\phi$, or A images 2224. Once the neural network model is well trained, a raw SSG image 2236 can be directly inputted to the neural network model 2240 and obtain the three-channel image comprising $I_0$, $\phi$, or A images 2248, as shown in FIG. 22B. In other embodiments, the input SSG image used in training is a plurality of both reference SSG images and object SSG images with the paired training images being a plurality of triples of ABS, DPC, and DF images. Therefore, the output images from the neural network model are three-channel contrast images.

In some embodiments, imaging errors and artifacts that are likely to occur in practice are added to the training SSG images as part of the training process. The loss function for supervised learning still compares the neural network output to the SSG images without artifacts. Errors and artifacts may include noise, moiré-like artifacts, stripes, or bad pixels.

Figure 23:
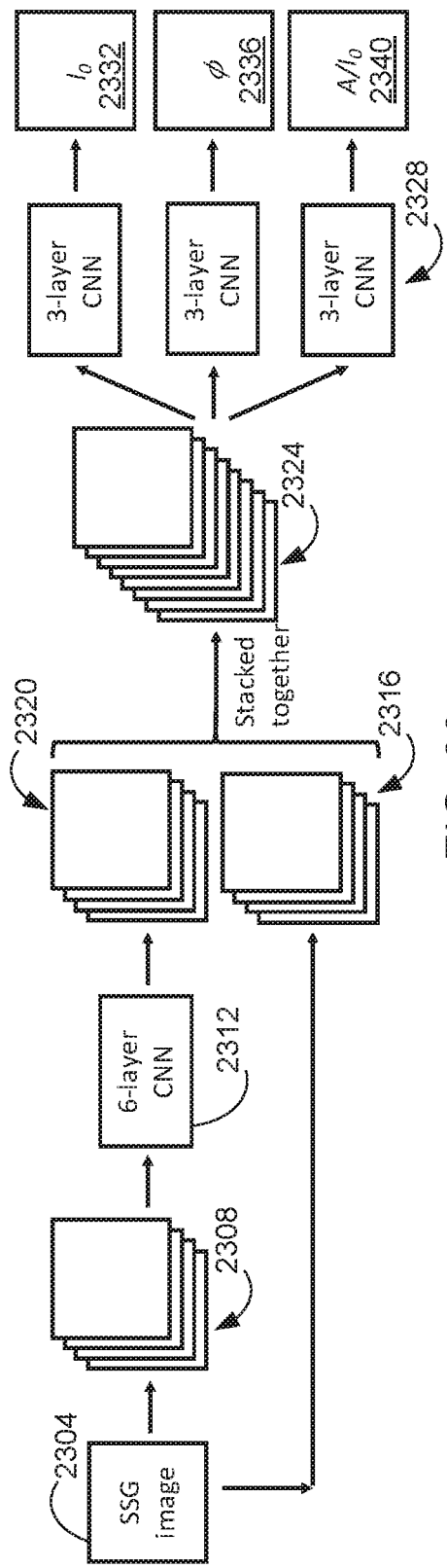
FIG. 23 shows a neural network model used in an embodiment.
Figure 24:
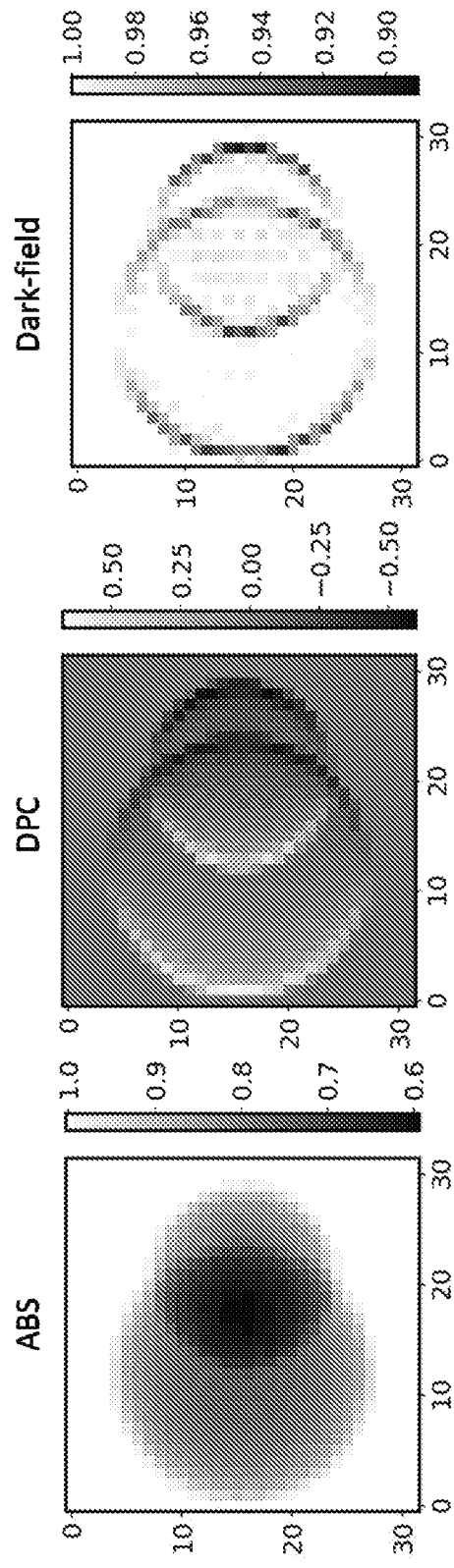
FIG. 24 shows the three-channel contrast images used a trained neural network in the embodiment of FIG. 23.

In one embodiment, as an example of using the neural network to reconstruct SSG images, shown in FIG. 23, we input a full SSG image 2304 taken with a 2×2 SSG unit cell and separate it into a stack of four image channels 2308 as described in FIG. 19C. The image stack is fed into a six-layer CNN 2312, which outputs a stack of four images 2320 with each image having the size as the original SSG image. The input SSG image is separated into four channels again 2316 and stack them together with the stacked image 2320 to form a stack of eight images 2324 to be input together into the next section of the neural network. The stack of eight images 2324 is input into each of the three branches of the next section of the neural network 2328, each of which is a three-layer CNN. The outputs from these three three-layer CNNs are respectively the $I_0$, $\phi$, and $A/I_0$ images (2332, 2336, and 2340), which collectively are the output of the entire neural network model shown in FIG. 23. A plurality of simulated spheres of various sizes, locations, and material properties was used in the training. After a few hours of training using 100,000 training samples, a test of the trained neural network was performed using the image of two overlapped spheres of two different materials. After processing together with a reference SSG image, the three-channel contrast images are shown in FIG. 24.

Figure 25:
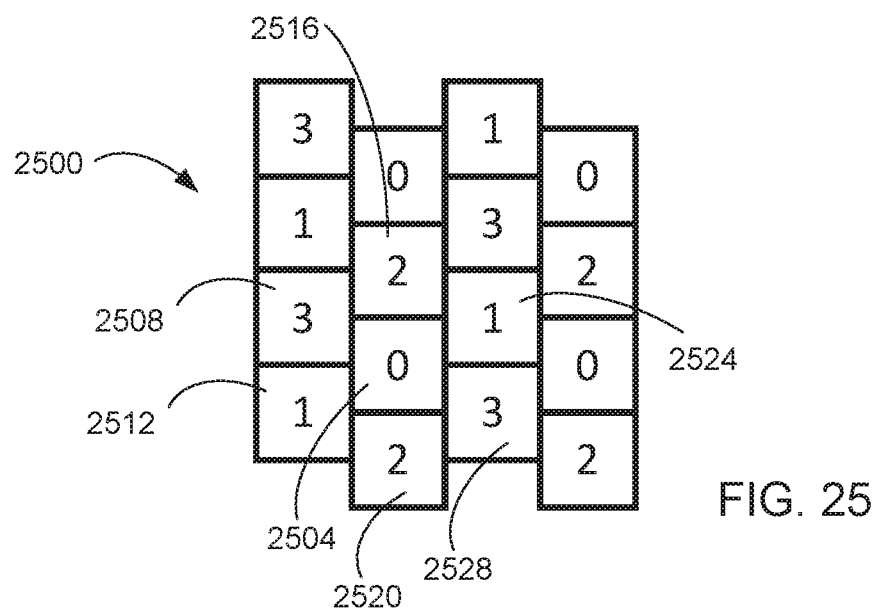
FIG. 25 is a schematic view of a staggered grating used in an embodiment.
Figure 26:
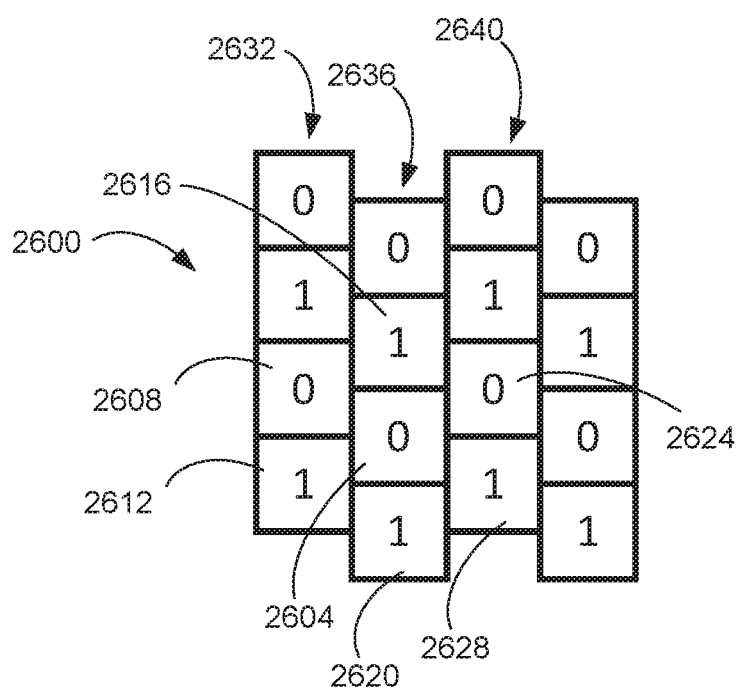
FIG. 26 is a schematic view of a staggered grating used in another embodiment.

In some embodiments, as shown in FIG. 25, the staggered grating pixels formed in the hexagonal lattice 2500 such that all adjacent grating pixels 2508, 2512, 2516, 2520, 2524, and 2528 in two dimensions do not have the same pattern as the grating pixel 2504. In other embodiments, as shown in FIG. 26, the staggered grating pixels formed in the hexagonal lattice 2600 such that the adjacent grating pixels 2616 and 2620 in one dimension on the same column 2636 or the same row do not have the same pattern as the grating pixel 2604. However, the adjacent grating pixels 2608 and 2624 in another dimension on the adjacent staggered columns 2632 and 2640 or rows can have the same pattern as the grating pixel 2604 as long as the adjacent grating pixels 2612 and the grating pixel 2608 on the next column 2632 do not have the same pattern, as an example. In this example, the two dimensions are orthogonal to each other.

While this invention has been described in terms of several preferred embodiments, there are alterations, permutations, modifications, and various substitute equivalents, which fall within the scope of this invention. It should also be noted that there are many alternative ways of implementing the methods and apparatuses of the present invention. It is therefore intended that the following appended claims be interpreted as including all such alterations, permutations, modifications, and various substitute equivalents as fall within the true spirit and scope of the present invention.

What is claimed is:

1. An X-ray analyzer grating configured for use in a one shot interferometric imaging system with image resolution recovery, the interferometric imaging system comprising an X-ray source and an X-ray detector with an X-ray fringe plane between the X-ray source and the X-ray detector, wherein an X-ray fringe pattern is formed at the X-ray fringe plane, wherein the X-ray analyzer grating located at the X-ray fringe plane, comprises:
   a plurality of grating pixels across two dimensions of the X-ray analyzer grating, wherein each grating pixel of the plurality of grating pixels has a shifted phase with respect to adjacent grating pixels in at least two dimensions to the grating pixel so that adjacent grating pixels in at least two dimensions have a shifted phase with respect to the grating pixel.

2. The X-ray analyzer grating, as recited in claim 1, wherein the interferometric imaging system is a one shot X-ray differential phase contrast imaging system.

3. The X-ray analyzer grating, as recited in claim 1, wherein each grating pixel of the plurality of grating pixels has a shifted phase with respect to all nearest neighbor grating pixels.

4. The X-ray analyzer grating, as recited in claim 1, wherein the X-ray analyzer grating has at least one of a one-dimensional grating pattern and a two-dimensional grating pattern.

5. The X-ray analyzer grating, as recited in claim 1, wherein the X-ray analyzer grating is one of planar, cylindrically curved, and spherically curved.

6. The X-ray analyzer grating, as recited in claim 1, wherein each of the grating pixels of the plurality of grating pixels is part of a unit cell of at least 2×2 grating pixels.

7. The X-ray analyzer grating, as recited in claim 6, wherein each of the grating pixels of the plurality of grating pixels is part of a unit cell of 2×3 grating pixels, 3×2 grating pixels, 3×3 grating pixels, 4×4 grating pixels.

8. An X-ray system for imaging an object in one shot, wherein the X-ray system comprises:
   an X-ray source;
   an X-ray detector with a plurality of detector pixels is spaced apart from the X-ray source;
      an X-ray grating between the X-ray source and the X-ray detector; and
      an analyzer grating between the X-ray grating and the X-ray detector, wherein the analyzer grating has a plurality of grating pixels across two dimensions, wherein a grating pixel has a phase shifted with respect to grating pixels adjacent in at least two dimensions to the grating pixel.

9. The X-ray system, as recited in claim 8, wherein the object is placed between the X-ray source and the analyzer grating.

10. The X-ray system, as recited in claim 8, wherein the X-ray source provides X-rays with energies ranging from 1 keV to 1 MeV.

11. The X-ray system, as recited in claim 8, wherein a plurality of grating pixels forms an at least 2×2 unit cell, wherein each grating pixel of the at least 2×2 unit cell has a pattern that is different from patterns of all other grating pixels of the at least 2×2 unit cell.

12. The X-ray system, as recited in claim 8, further comprising a computer system connected to the X-ray detector, comprising:
   a processor; and
   computer readable media, comprising:
      computer readable code for receiving X-ray detection data for a single shot filtered by the analyzer grating from the X-ray detector; and
      computer readable code for using the X-ray detection data for the single shot filtered by the analyzer grating to create an image of the object by reconstructing each detector pixel from the single shot.

13. The X-ray system, as recited in claim 8, wherein the X-ray system is part of a computed tomography system.

14. The X-ray system, as recited in claim 8, wherein the X-ray system has an X-ray fringe plane between the X-ray source and the X-ray detector, wherein an X-ray fringe pattern is formed at the X-ray fringe plane and wherein the analyzer grating is located sufficiently close to the X-ray fringe plane to allow for a measurement of the X-ray fringe pattern using the analyzer grating.

15. The X-ray system, as recited in claim 14, wherein the X-ray fringe pattern has a pitch and wherein the analyzer grating has a pitch, wherein the pitch of the analyzer grating is within 5% of the pitch of the X-ray fringe pattern.

16. The X-ray system, as recited in claim 12, wherein the computer readable code for using the X-ray detection data for the single shot to create an image by reconstructing each detector pixel from the single shot uses resolution recovery comprising at least one of simple curve fitting, spatially varying curve fitting, and artificial neural network reconstruction to create the image.

17. The X-ray system, as recited in claim 8, wherein the X-ray detector has a detector pixel size in a range from 500 nanometers to 50 millimeters.

18. The X-ray system, as recited in claim 8, wherein the X-ray detector, wherein each grating pixel of the plurality of grating pixels has 1 adjacent detector pixel, 1×2 adjacent detector pixels, 2×1 adjacent detector pixels, 2×2 adjacent detector pixels, 3×3 adjacent detector pixels, or a plurality of adjacent detector pixels.

19. A method for X-ray imaging an object in an X-ray system comprising an X-ray source, an X-ray detector, an X-ray grating between the X-ray source and object, and an analyzer grating between the X-ray grating and the X-ray detector, wherein the analyzer grating has a plurality of grating pixels across two dimensions, wherein each grating pixel has a shifted phase with respect to grating pixels adjacent to the grating pixel in at least two dimensions, the method comprising:
   passing X-rays from the X-ray source through the object, the X-ray grating and the analyzer grating to the X-ray detector in a single shot, wherein the analyzer grating is not moved;
   receiving X-ray detection data from the X-ray detector; and
   using the X-ray detection data to create at least one of an intensity image, an amplitude image, and a phase image with image resolution recovery of the object by reconstructing each detector pixel from the single shot.

20. The method, as recited in claim 19, wherein using the X-ray detection data to create an image of the object, comprises:
   determining variations in recorded X-ray detection data corresponding to adjacent grating pixels for a single shot; and using the determined variations in recorded X-ray detection data corresponding to adjacent grating pixels for the single shot and data from a reference shot to create at least one of an absorption contrast image, differential phase contrast image, and dark-field contrast image with image resolution recovery of the object.

21. The method, as recited in claim 19, wherein a plurality of grating pixels forms a plurality of unit cells of an at least 2×2 grating pixel, wherein each unit cell of the plurality of unit cells has a grating pixel that is shifted from patterns of all other grating pixels of the unit cell.

22. The method, as recited in claim 19, wherein the X-ray system is part of a computed tomography system.

23. The method, as recited in claim 19, wherein the X-ray system has an X-ray fringe plane between the X-ray source and the X-ray detector, wherein an X-ray fringe pattern is formed at the X-ray fringe plane and wherein the analyzer grating is located sufficiently close to the X-ray fringe plane to allow for a measurement of the X-ray fringe pattern using the analyzer grating.

24. The method, as recited in claim 23, wherein the X-ray fringe pattern has a pitch and wherein the analyzer grating has a pitch, wherein the pitch of the analyzer grating is within 5% of the pitch of the X-ray fringe pattern.

25. The method, as recited in claim 19, wherein the using the X-ray detection data to create at least one of the intensity image, the amplitude image, and the phase image with image resolution recovery of the object uses artificial intelligence.

26. An X-ray system for imaging an object in one shot, wherein the X-ray system comprises:
an X-ray source;
an X-ray detector with a plurality of detector pixels spaced apart from the X-ray source;
an X-ray grating between the X-ray source and the X-ray detector; and
an analyzer grating between the X-ray grating and the X-ray detector, wherein the analyzer grating has a plurality of grating pixels across two dimensions, wherein a grating pixel has a shifted phase with respect to adjacent grating pixels in all directions.

27. The X-ray system, as recited in claim 26, wherein the two dimensions comprises a first dimension and a second dimension wherein the first dimension is orthogonal to the second dimension.

28. A method for X-ray imaging an object in an X-ray system comprising an X-ray source, an X-ray detector, an X-ray grating between the X-ray source and object, and an analyzer grating between the X-ray grating and the X-ray detector, wherein the analyzer grating has a plurality of grating pixels across at least two dimensions, wherein each grating pixel has a phase shift with grating pixels adjacent to the grating pixel in the at least two dimensions, the method comprising:
passing X-rays from the X-ray source through the object, the X-ray grating, and the analyzer grating to the X-ray detector for a single shot, wherein the analyzer grating is not moved;
receiving X-ray detection data from the X-ray detector for the single shot; and
applying artificial intelligence to the X-ray detection data for the single shot to create at least one of an intensity image, an amplitude, and a phase image with image resolution recovery of the object by reconstructing each detector pixel from the single shot.

29. The method, as recited in claim 28, wherein the applying artificial intelligence to the X-ray detection data for the single shot also uses X-ray detection data from a reference shot to create at least one of the absorption contrast, differential phase contrast, and dark-field contrast images of the object with image resolution recovery.

30. The method, as recited in claim 28, wherein the X-ray grating is one of planar, cylindrically curved, and spherically curved.

31. The X-ray analyzer grating, as recited in claim 1, wherein each grating pixel corresponds to a single adjacent X-ray detector pixel.

* * * * *